US011714093B2

(12) United States Patent
Steinhoff et al.

(10) Patent No.: US 11,714,093 B2
(45) Date of Patent: Aug. 1, 2023

(54) METHOD FOR PREDICTION OF RESPONSE TO CARDIOVASCULAR REGENERATION BASED ON DETECTING THE AMOUNT OF BIOMARKERS

(71) Applicant: Universität Rostock, Rostock (DE)

(72) Inventors: Gustav Steinhoff, Rethwisch-Börgerende (DE); Julia Nesteruk, Kaiserslautern (DE); Markus Wolfien, Kritzmow (DE)

(73) Assignee: Universität Rostock, Rostock (DE)

( * ) Notice: Subject to any disclaimer, the term of this patent is extended or adjusted under 35 U.S.C. 154(b) by 386 days.

(21) Appl. No.: 16/631,756

(22) PCT Filed: Jul. 16, 2018

(86) PCT No.: PCT/EP2018/069307
§ 371 (c)(1),
(2) Date: Jan. 16, 2020

(87) PCT Pub. No.: WO2019/016156
PCT Pub. Date: Jan. 24, 2019

(65) Prior Publication Data
US 2020/0174020 A1    Jun. 4, 2020

(30) Foreign Application Priority Data
Jul. 18, 2017 (DE) ............... 10 2017 116 204.6

(51) Int. Cl.
| G01N 33/68 | (2006.01) |
| G01N 33/50 | (2006.01) |
| G01N 33/53 | (2006.01) |
| G01N 33/74 | (2006.01) |
| C12Q 1/686 | (2018.01) |
| G16B 40/00 | (2019.01) |
| C12Q 1/6883 | (2018.01) |

(52) U.S. Cl.
CPC ......... *G01N 33/6893* (2013.01); *C12Q 1/686* (2013.01); *G01N 33/5094* (2013.01); *G01N 33/53* (2013.01); *G01N 33/74* (2013.01); *C12Q 1/6883* (2013.01); *G01N 33/5005* (2013.01); *G01N 2333/475* (2013.01); *G01N 2333/50* (2013.01); *G01N 2333/505* (2013.01); *G01N 2333/535* (2013.01); *G01N 2333/58* (2013.01); *G01N 2333/78* (2013.01); *G01N 2800/323* (2013.01); *G01N 2800/324* (2013.01); *G01N 2800/325* (2013.01); *G01N 2800/52* (2013.01); *G01N 2800/60* (2013.01); *G16B 40/00* (2019.02)

(58) Field of Classification Search
CPC .............. G01N 33/68; G01N 33/6893; G01N 33/5005; G01N 2800/52; G01N 33/53; G01N 33/5094; G01N 33/74; G01N 2800/323; G01N 2800/324; G01N 2800/325; C12Q 1/686
See application file for complete search history.

(56) References Cited

U.S. PATENT DOCUMENTS

| 9,446,076 B2 | 9/2016 | Gaussin et al. |
| 2009/0280094 A1 | 11/2009 | Matsumoto et al. |
| 2010/0129440 A1 | 5/2010 | Zhao et al. |
| 2011/0256105 A1 | 10/2011 | Marban et al. |
| 2013/0095060 A1 | 4/2013 | Hsieh et al. |
| 2013/0108594 A1 | 5/2013 | Martin-Rendon et al. |
| 2015/0111224 A1 | 4/2015 | Arslan |
| 2015/0337031 A1 | 11/2015 | Mauen et al. |
| 2017/0010283 A1 | 1/2017 | Karl et al. |
| 2019/0277861 A1 | 9/2019 | Karl et al. |

FOREIGN PATENT DOCUMENTS

| CN | 101940594 A | 1/2011 |
| CN | 102438636 A | 5/2012 |
| EP | 2 362 942 B1 | 6/2017 |
| JP | 2007-511206 A | 5/2007 |
| JP | 2013-520509 A | 6/2013 |
| JP | 2016-508129 A | 3/2016 |
| JP | 2017-512988 A | 5/2017 |
| WO | 2005/038454 A1 | 4/2005 |
| WO | 2007/142288 A1 | 12/2007 |
| WO | 2009/061382 A2 | 5/2009 |
| WO | 2011/106365 A1 | 9/2011 |
| WO | 2015/144767 A1 | 10/2015 |

OTHER PUBLICATIONS

Reboucas et al, 2016. Arq Bras Cardiol. 107(3)271-275.*
Morikawa et al, 2016. Cold Spring Harbor Perspectives in Biology. 8:a021873; 26 pages as printed.*
Clerc, 2016. Glycoconj J. 33: 309-343.*
Libby et al., 2015. Arterioscler Thromb Vasc Biol. 35:2491-2495.*
International Search Report issued in PCT/EP2018/069307; dated Sep. 4, 2018.
Database Accession No. NP_001020537.2; GenBank; Apr. 5, 2020; pp. 1-5; NCBI.
Database Accession No. p01588.1; GenBank; Oct. 16, 2019; pp. 1-9; NCBI.
Database Accession No. p02778.2; GenBank; Nov. 13, 2019; pp. 1-6; NCBI.
Database Accession No. p05231.1; GenBank; Nov. 13, 2019; pp. 1-7; NCBI.
Database Accession No. p17936.1; GenBank; Oct. 16, 2019; pp. 1-6; NCBI.

(Continued)

*Primary Examiner* — Zachary C Howard
(74) *Attorney, Agent, or Firm* — Studebaker & Brackett PC

(57) ABSTRACT

The present invention relates to a method for prediction of response to cardiovascular regeneration comprising the use of biomarkers. Further, the present invention relates to a combination of the biomarkers for use in a method for prediction of response to cardiovascular regeneration, a computer device to perform a method according to the present invention and a device adapted for carrying out the inventive method.

18 Claims, 4 Drawing Sheets

(56) References Cited

OTHER PUBLICATIONS

Figure 1:
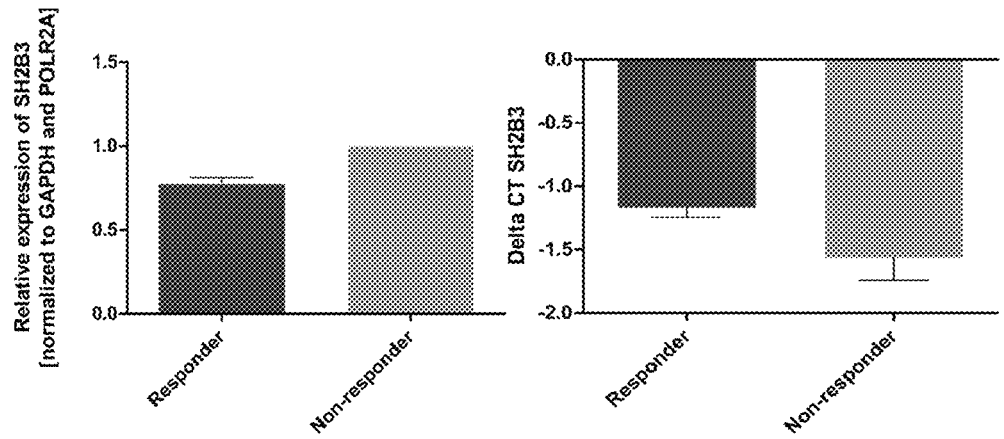

Bartunek, Jozef et al.; "Cardiopoietic cell therapy for advanced ischaemic heart failure: results at 39 weeks of the prospective, randomized, double blind, sham-controlled CHART-1 clinical trial"; European Heart Journal; Dec. 23, 2016; pp. 648-660; doi:10.1093/eurheartj/ehw543.

Bhatnagar, Aruni et al.; "Bone marrow cell characteristics associated with patient profile and cardiac performance outcomes in the LateTIME-Cardiovascular Cell Therapy Research Network (CCTRN) trial"; American Heart Journal Sep. 2016; pp. 142-150; vol. 179.

Booth, Valerie et al.; "The CXCR3 Binding Chemokine IP-10/CXCL10: Structure and Receptor Interactions"; Biochemistry; 2002; pp. 10418-10425; vol. 41, No. 33.

Boron, Walter F. et al.; "Medical Physiology: A Cellular and Molecular Approach"; Saunders; 2012; Updated Second Edition; p. 1097.

Chow, Sheryl L. et al.; "Role of Biomarkers for the Prevention, Assessment, and Management of Heart Failure: A Scientific Statement From the American Heart Association"; Circulation, Apr. 26, 2017; pp. e1054-e1091; vol. 135, No. 22; ISSN 0009-7322, XP055502426, DOI: http://dx.doi.org/10.1161/CIR.0000000000000490.

Cohen-Solal, Alain et al.; "Prognostic markers of acute decompensated heart failure: the emerging roles of cardiac biomarkers and prognostic scores"; Archives of Cardiovascular Diseases; 2015; pp. 64-74; vol. 108, No. 1.

Contreras, Ariadna et al.; "Identification of cardiovascular risk factors associated with bone marrow cell subsets in patients with STEMI: a biorepository evaluation from the CCTRN Time and LateTIME clinical trials"; Basic Res Cardiol; Jan. 2017; p. 3; vol. 112, No. 1.

Forman, George et al.; "Learning from Little: Comparison of Classifiers Given Little Training"; 2004; doi 10.1007/978-3-540-30116-5_17.

Henry, Timothy D. et al.; "Consistently Inconsistent-Bone Marrow Mononuclear Stem Cell Therapy Following Acute Myocardial Infarction: A Decade Later"; Circulation Research; Jul. 22, 2016; pp. 404-406; vol. 119.

Hofmann, Wolf-K et al.; "Relation between resistance of Philadelphia-chromosome-positive acute lymphoblastic eukaemia to the tyrosine kinase inhibitor STI571 and gene-expression profiles: a gene-expression study"; The Lancet; Feb. 9, 2002; pp. 481-486; vol. 359, No. 9305.

Kuhn, Max; "Building Predictive Models in R Using the caret Package"; Journal of Statistical Software; Nov. 2008; pp. 1-26; vol. 28, No. 5.

Kwon, Sang-Mo et al.; "Pivotal Role of Lnk Adaptor Protein in Endothelial Progenitor Cell Biology for Vascular Regeneration"; Circulation Research; Apr. 24, 2009; pp. 969-977; vol. 104, No. 8.

Li, Yijin et al.; "Cloning and Characterization of Human Lnk, an Adaptor Protein with Pleckstrin Homology and Src Homology 2 Domains that Can Inhibit T Cell Activation"; The Journal of Immunology; 2000; pp. 5199-5206; vol. 164, No. 10.

Nasseri, Boris A. et al.; "Autologous CD133+ bone marrow cells and bypass grafting for regeneration of schaemic myocardium: the Cardio133 trial"; European Heart Journal; 2014; pp. 1263-1274; vol. 35, No. 19.

Needleman, Saul B. et al.; "A General Method Applicable to the Search for Similarities in the Amino Acid Sequence of Two Proteins"; J. Mol. Biol.; 1970; p. 443; vol. 48.

O'Brien, Ralph G. et al.; "Unified Power Analysis for t-Tests through Multivariate Hypotheses"; In L K Edward (Ed.) Applied Analysis of Variance in the Behavioral Sciences; 1993; New York; Marcel Dekker.

Pearson, William R. et al.; "Improved Tools for Biological Sequence Comparison"; Proc. Natl. Acad. Sci. USA; Apr. 1988; p. 2444; vol. 85.

Saeb, Amr T. M. et al.; "The Impact of Evolutionary Driving Forces on Human Complex Diseases: A Population Genetics Approach"; Scientifica; Cairo; 2016; pp. 1-10; vol. 2016; Article ID 2079704.

Smith, Temple F. et al.; "Comparison of Biosequences"; Advances in Applied Mathematics; 1981; p. 482; vol. 2.

Stamm, Christof et al.; "Autologous bone-marrow stem-cell transplantation for myocardial regeneration"; The Lancet; Jan. 4, 2003; pp. 45-46; vol. 361, No. 9351.

Stamm, Christof et al.; "Intramyocardial delivery of CD 133+ bone marrow cells and coronary artery bypass grafting for chronic ischemic heart disease: Safety and efficacy studies"; The Journal of Thoracic and Cardiovascular Surgery; Mar. 2007; pp. 717-725; vol. 133, No. 3.

Taylor, Doris A. et al.; "Identification of Bone Marrow Cell Subpopulations Associated With Improved Functional Outcomes in Patients With Chronic Left Ventricular Dysfunction: An Embedded Cohort Evaluation of the FOCUS-CCTRN Trial"; Cell Transplant; Nov. 1, 2016; pp. 1675-1687; vol. 25, No. 9.

Thweatt, Ray et al.; "Analysis of the primary structure of insulin-like growth factor binding protein-3 cDNA from Werner syndrome fibroblasts"; DNA Sequence; 1993; pp. 43-46; vol. 4, No. 1.

Tischer, Edmund et al.; "The Human Gene for Vascular Endothelial Growth Factor: Multiple Protein Forms Are Encoded Through Alternative Exon Splicing"; The Journal of Biological Chemistry; Jun. 25, 1991; pp. 11947-11954; vol. 266, No. 18.

Tse, Hung-Fat et al.; "Angiogenesis in ischaemic myocardium by intramyocardial autologous bone marrow mononuclear cell implantation"; The Lancet; Jan. 4, 2003; pp. 47-49; vol. 361, No. 9351.

Van Der Maaten, Laurens et al.; "Visualizing Data using t-SNE"; Journal of Machine Learning Research; 2008; pp. 2579-2605; vol. 9.

Werner, Nikos et al.; "Circulating Endothelial Progenitor Cells and Cardiovascular Outcomes"; The New England Journal of Medicine; Sep. 8, 2005; pp. 999-1007; vol. 353, No. 10.

Wong, GG et al.; "Interleukin 6: Identification as a Hematopoietic Colony-Stimulating Factor" ABSTRACT; Behring Institute Mitteilungen; Aug. 1, 1988; pp. 40-47; vol. 83.

Yanagawa, Shin-Ichi et al.; "Isolation of Human Erythropoietin with Monoclonal Antibodies"; The Journal of Biological Chemistry; 1984; pp. 2707-2710; vol. 259, No. 5.

Zweig, Mark H. et al.; "Receiver-Operating Characteristic (ROC) Plots: A Fundamental Evaluation Tool in Clinical Medicine"; Clinical Chemistry, 1993; pp. 561-577; vol. 39, No. 4.

Yamasaki Motonari et al.; "Coronary artery bypass grafting for moderately or severely impaired left ventricular function"; J Jpn Coron Assoc 2011; 17; pp. 8-15.

An Office Action mailed by the Japanese Patent Office dated Jun. 7, 2022, which corresponds to Japanese Patent Application No. 2020-502119 and is related to U.S. Appl. No. 16/631,756; with English language translation.

David Zisa et al., "Vascular endothelial growth factor (VEGF) as a key therapeutic trophic factor in bone marrow mesenchymal stem cell-mediated cardiac repair", Biochem Biophys Res Commun., vol. 390, No. 3, Dec. 18, 2009, pp. 834-838.

Francois Haddad et al., "Immunologic Network and Response to Intramyocardial CD34+ Stem Cell Therapy in Patients With Dilated Cardiomyopathy", Journal of Cardiac Failure, vol. 21, No. 7, Apr. 8, 2015, pp. 572-582. X.

* cited by examiner

SH2B3 expression analysis

Three-dimensional t-SNE calculation

ML prediction results for pre- and postoperative time points (0 to 180 days)

METHOD FOR PREDICTION OF RESPONSE TO CARDIOVASCULAR REGENERATION BASED ON DETECTING THE AMOUNT OF BIOMARKERS

The present invention relates to a method for prediction of response to cardiovascular regeneration comprising the use of biomarkers. Further, the present invention relates to a combination of the biomarkers for use in a method for prediction of response to cardiovascular regeneration, a computer device to perform a method according to the present invention and a device adapted for carrying out the inventive method.

Regenerative therapies for the repair of heart tissue have been at the forefront of preclinical and clinical development in the last 16 years. Among the different approaches the direct application of bone marrow stem cells in heart tissue still has the most dedicated clinical developmental attention since the first-in-man application in 2001 and the initial promising clinical trials (Stamm C, Westphal B, Kleine H D, et al. Lancet. 2003; 361(9351):45-46; Tse H F, Kwong Y L, Chan J K, Lo G, Ho C L, Lau C P. Lancet 2003; 361(9351): 47-9; Stamm C, Kleine H D, Choi Y H, et al. J Thorac Cardiovasc Surg 2007; 133(3):717-25). Yet, in these trials, clinically relevant improvements of LVEF (Left Ventricular Ejection Fraction) as well as non-responsive patients could be observed both in treatment and placebo groups (Timothy D H, Lem M, Jay H T, Circulation Research 2016; 119:404-406; Nasseri B A, Ebell W, Dandel M, et al. Eur Heart J. 2014, 35(19):1263-74; Bartunek J, Terzic A, Davison B A et al. Eur. Heart J. 2016 Dec. 23. pii: ehw543. doi: 10.1093/eurheartj/ehw543).

This has raised the question of induction for regenerative mechanisms independent of stem cell application and potential suppressive factors of vascular repair associated with $CD34^+$ Endothelial Progenitor Cells (EPC) (Werner N, Kosiol S, Schiegl T, et al. N Engl J Med. 2005; 353(10): 999-1007). In respect of the recent published assumption it should be noted that the pivotal role of $CD133/CD34^+$ peripheral circulating EPC could be related to the lack of cardiac regeneration (Taylor D A, Perin E C, Willerson J T, et al. Cell Transplant 2016; 25(9):1675-1687; Bhatnagar A, Bolli R, Johnstone B H, et al. Am Heart J 2016; 179:142-50; Contreras A, Orozco A F, Resende M, et al. Basic Res Cardiol 2017; 112(1):3).

Thus, the mechanism of cardiac regeneration and the role of bone marrow stem cell-regulated angiogenesis still remain unsolved.

The inventors have now identified a method for prediction of response to cardiovascular regeneration comprising the determination of biomarkers. The present invention is thus directed to a method for prediction of response to cardiovascular regeneration comprising the determination of biomarkers, according to claim 1 of the present application. Further, the present invention relates to a combination of the biomarkers for use in a method for prediction of response to cardiovascular regeneration, a computer device to perform such a method and a device adapted for carrying out the inventive method.

The present invention is thus directed to a method for prediction of response to cardiovascular regeneration, wherein the method comprises (i) determining in a sample of a subject the amount of each of the following biomarkers, wherein the biomarkers are selected from the group of Growth factor, Lymphocyte adapter protein, Glycoprotein, brain natriuretic peptide (BNP), circulating endothelial progenitor cells (EPC), circulating endothelial cells (CEC), circulating thrombocytes, circulating mononuclear cells (MNC) and subpopulations, and receptor/ligand expression on MNC subpopulations, (ii) comparing the determined amounts to a baseline value and/or a reference, (iii) predicting, based on the results of the comparison, whether a response to cardiovascular repair in the subject is to be expected, not expected or is ambivalent.

Preferably, the method of the present invention is an ex vivo method. Moreover, it may comprise steps in addition to those explicitly mentioned above. For example, further steps may relate to sample pre-treatments or further evaluations or uses of the results obtained by the method. The method may be carried out manually or assisted by automation. Preferably, step (i) may in total or in part be assisted by automation, e.g. by a suitable robotic and sensory equipment. Steps (ii) and/or (iii) may be assisted by data processing units which carry out the respective comparisons and/or predictions.

Advantageously, by using the method of the present invention prediction accuracy of response to cardiovascular regeneration can be improved to more than about 80%, more preferably to more than about 85%, even more preferably to more than about 90%.

The term "predicting" as used herein means assessing the probability according to which a subject will benefit from cardiac stem cell therapy in that there is a functional improvement of the cardiovascular system as defined elsewhere herein in detail after the said cardiac therapy.

As will be understood by those skilled in the art, such an assessment is usually not intended to be correct for 100% of the subjects to be diagnosed. The term, however, requires that the assessment is correct for a statistically significant portion of the subjects (e.g. a cohort in a cohort study). Whether a portion is statistically significant can be determined without further ado by the person skilled in the art using various well known statistic evaluation tools, e.g., by determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.0001.

The term "cardiovascular regeneration" as used herein includes the regeneration and/or treatment and/or improvement of diseases related to the cardiovascular system.

The term "biomarker" refers to molecules, the presence, absence or amount of which correlates with medical conditions or predispositions. Biomarkers may be any molecules and/or cells or subpopulations thereof which occur in the subject. Typically, biomarkers are proteins, peptides, small molecules or nucleic acids, such as DNAs or RNAs, or cells and subpopulations thereof. In accordance with the present invention, the term, preferably, refers to proteins and peptides, i.e. to growth hormones such as VEGF, FGF or Erythropoietin, to lymphocyte adapter protein such as SH2B3, to glycoproteins such as Vitronectin or GCSF, to brain natriuretic peptide such as NT-proBNP, to cytokines such as TNF, to interleukins such as IL-6, IL-8 or IL-10, to interferons such as human interferon gamma-induced protein 10, to insulin-like-growth-factor-binding proteins such as insulin-like-growth-factor-binding protein-2 and/or insulin-like-growth-factor-binding protein-3, the Insulin-like growth factor is preferably selected from IGF2, to chemokine proteins such as SDF-1 and to multi-protein E3 ubiquitin ligase complexes such as SCF.

Further, in accordance with the present invention, biomarkers refer to cells and subpopulations thereof, i.e. to circulating endothelial progenitor cells (EPC), to possess or not possess on their surface cluster of differentiation (CD), such as, e.g. CD45, CD117, CD184, CD133 and/or CD146, circulating endothelial cells (CEC) to possess or not possess on their surface CD31, CD133, CD146, CD105 and/or CD34, circulating thrombocytes, circulating mononuclear cells (MNC) and subpopulations, and receptor/ligand expression on MNC subpopulations to possess or not possess CD184, CD309, cell adhesion molecules (CAM) and/or integrin receptors.

Determining the amount of a biomarker referred to in this specification relates to measuring the amount or concentration, preferably, semi-quantitatively or quantitatively. Measuring can be done directly or indirectly. Direct measuring relates to measuring the amount or concentration of the biomarker based on a signal which is obtained from the biomarker itself and the intensity of which directly correlates with the number of molecules of the biomarker present in the sample. Such a signal—sometimes referred to herein as intensity signal—may be obtained, e.g. by measuring an intensity value of a specific physical or chemical property of the biomarker. Indirect measuring includes measuring of a signal obtained from a secondary component (i.e. a component not being the biomarker itself) or a biological read out system, e.g. measurable cellular responses, ligands, labels, or enzymatic reaction products.

In accordance with the present invention, determining the amount of a biomarker can be achieved by all known means for determining the amount of a peptide, a protein, a small molecule, nucleic acids such as DNAs or RNAs or a cell or subpopulations thereof, in a sample. Said means comprise immunoassays and methods which may utilize labelled molecules in various sandwich, competition, or other assay formats. Such assays are, preferably, based on detection agents such as antibodies which specifically recognize the biomarker to be determined. The detection agents shall be either directly or indirectly capable of generating a signal indicating the presence or absence of the biomarker. Moreover, the signal strength can, preferably, be correlated directly or indirectly (e.g. reverse-proportional) to the amount of biomarker present in a sample. Further suitable methods comprise measuring a physical or chemical property specific for the biomarker such as its precise molecular mass or NMR spectrum. Said methods comprise, preferably, biosensors, optical devices coupled to immunoassays, FACS analysis, biochips, analytical devices such as mass-spectrometers, NMR-analysers, or chromatography devices. Further, methods include micro-plate ELISA-based methods, fully-automated or robotic immunoassays, enzymatic Cobalt binding assays, and latex agglutination assays.

Preferably, determining the amount of a biomarker comprises the steps of (a) contacting a cell capable of eliciting a cellular response the intensity of which is indicative of the amount of the biomarker with the said biomarker for an adequate period of time, (b) measuring the cellular response. For measuring cellular responses, the sample or processed sample is, preferably, added to a cell culture and an internal or external cellular response is measured. The cellular response may include the measurable expression of a reporter gene or the secretion of a substance, e.g. a peptide, polypeptide, or a small molecule. The expression or substance shall generate an intensity signal which correlates to the amount of the biomarker.

Also preferably, determining the amount of a biomarker comprises the step of measuring a specific intensity signal obtainable from the biomarker in the sample. As described above, such a signal may be the signal intensity observed at an m/z variable specific for the biomarker observed in mass spectra or an NMR spectrum specific for the biomarker.

The term "amount" as used herein encompasses the absolute amount of a biomarker, the relative amount or concentration of said biomarker as well as any value or parameter which correlates thereto or can be derived therefrom. Such values or parameters comprise intensity signal values from all specific physical or chemical properties obtained from said peptides by direct measurements, e.g. intensity values in mass spectra or NMR spectra. Moreover, encompassed are all values or parameters which are obtained by indirect measurements specified elsewhere in this description, e.g. response levels determined from biological read out systems in response to the peptides or intensity signals obtained from specifically bound ligands. It is to be understood that values correlating to the aforementioned amounts or parameters can also be obtained by all standard mathematical operations and can be used without dimensions, e.g. in scoring systems as described elsewhere herein.

The term "comparing" as used herein encompasses comparing the amount of the biomarker comprised by the sample to be analysed with an amount of a suitable reference source specified elsewhere in this description. It is to be understood that comparing as used herein refers to a comparison of corresponding parameters or values, e.g., an absolute amount is compared to an absolute reference amount while a concentration is compared to a reference concentration or an intensity signal obtained from a test sample is compared to the same type of intensity signal of a reference sample. However, in accordance with the present invention it is also envisaged to calculate a value based on the measured amounts of the biomarkers. Said value is compared to reference intervals which have been derived from a multivariate discriminant analysis performed on amounts from a collective of subjects comprising pre-defined responders and non-responders to cardiac stem cell therapy. Further details may be found in the accompanying examples, below.

The comparison referred to in the method of the present invention may be carried out manually or computer assisted. For a computer assisted comparison, the value of the determined amount may be compared to values corresponding to suitable references which are stored in a database by a computer program. The computer program may further evaluate the result of the comparison, i.e. automatically provide the desired assessment in a suitable output format. Preferably, such an assessment is performed by machine learning (ML). Based on the comparison of the determined amounts and the reference, it is possible to predict a response to cardiac regeneration, e.g. a functional improvement of the heart after cardiac stem cell therapy. In particular, it shall be possible to predict whether there is a high probability (i.e. the subject will be a responder), a low probability (i.e. the subject will be a non-responder) or the subject is ambivalent. Therefore, the reference amount is to be chosen so that either a difference or a similarity in the compared amounts allows identifying those test subjects which belong into the group of subjects exhibiting a symptom of acute inflammation having either an ischemic or non-ischemic cerebral damage. The method allows either excluding (rule-out) or identifying (rule-in) a subject as a subject suffering from (i) an ischemic cerebral damage or (ii) a non-ischemic cerebral damage.

The term "reference" as used herein refers to a value, threshold or interval based on amounts of the biomarkers which allow for allocation of a subject into either the group of subjects which can be expected to benefit from the cardiac therapy, which can be expected not to benefit from the cardiac therapy or those which are ambivalent.

Such a reference can be a threshold amount which separates these groups from each other. A suitable threshold amount separating the two groups can be calculated without further ado by the statistical tests referred to herein elsewhere based on amounts of the biomarkers from either a subject or group of subjects known to benefit from cardiac therapy or a subject or group of subjects known not to benefit from said therapy or those which are known to be ambivalent.

A reference can, in principle, also be calculated for a cohort of subjects as specified above based on the average or mean values for a given biomarker by applying standard statistically methods. In particular, accuracy of a test such as a method aiming to diagnose an event, or not, is best described by its receiver-operating characteristics (ROC) (see especially Zweig 1993, Clin. Chem. 39:561-577). Accordingly, the reference to be used for the aforementioned method of the present invention may be generated by establishing a ROC for said cohort as described above and deriving a threshold amount therefrom. Dependent on a desired sensitivity and specificity for a diagnostic method, the ROC plot allows deriving suitable thresholds.

The term "sample" refers to a sample of a body fluid, and preferably, to a sample of (whole) blood, plasma or serum. The term, however, also encompasses all samples which are derived from the aforementioned whole blood, plasma or serum by, e.g. pre-treatment steps such as fractions of blood, plasma or serum obtained by, e.g. partial purification.

The term "subject" as used herein refers to an animal, preferably, a mammal and, most preferably, a human. The subject shall be in need of cardiac therapy. Preferably, a subject in need for cardiac therapy suffers from a cardiac disease such as heart failure or coronary artery disease, e.g. after myocardial infarction, and, more preferably, from heart failure.

The prediction made according to the method of the invention also allows for assessing whether the probability is high and, thus, it is expected that a functional improvement of the cardiac system in a subject occurs, or whether the probability is such that the therapy success is ambivalent or whether the probability is low and, thus, it is expected that a functional improvement of the cardiac system in a subject will not occur.

The present invention further relates to a combination of biomarkers selected from the group of Growth factor, Lymphocyte adapter protein, Glycoprotein, brain natriuretic peptide (BNP), circulating endothelial progenitor cells (EPC), circulating endothelial cells (CEC), circulating thrombocytes, circulating mononuclear cells and subpopulations, and receptor/ligand expression on MNC subpopulations for use in a method for prediction of response to cardiovascular regeneration.

Also, the present invention is directed to a computer device comprising a processor and a memory encoding one or more machine learning (ML) models coupled to the processor, wherein said programs cause the processor to perform a method, said method comprising
 (i) comparing the determined amounts of the biomarker/s according to the present invention to a baseline value and/or a reference,
 (ii) predicting, based on the results of the comparison, whether a response to cardiovascular regeneration in the subject is to be expected, not expected or is ambivalent.

In addition, the present invention pertains to a device adapted for carrying out the inventive method, comprising
 (i) an analysing unit for determining in a sample of the subject the amount of each of the biomarkers according to the present invention, and
 (ii) a computer device according to the present invention (as detailed above).

The term "device" as used herein relates to a system comprising the aforementioned units operatively linked to each other as to allow the diagnosis according to the methods of the invention. Preferred detection agents which can be used for the analysing unit are disclosed elsewhere herein. Preferred detection agents are antibodies or other proteins that specifically bind to the biomarker(s) and form detectable complexes. The analysing unit, preferably, comprises said detection agents in immobilized form on a solid support which is to be contacted to the sample comprising the biomarkers the amount of which is to be determined. Moreover, the analysing unit can also comprise a detector which determines the amount of detection agent which is specifically bound to the biomarker(s). The determined amount can be transmitted to the evaluation unit. Said evaluation unit comprises a data processing element, such as a computer, with an implemented algorithm for carrying out a comparison between the determined amount and a suitable reference. Suitable references can be derived from samples of subjects to be used for the generation of reference amounts as described elsewhere herein above. The results may be given as output of parametric diagnostic raw data, preferably, as absolute or relative amounts. It is to be understood that these data will need interpretation by the clinician. However, also envisaged are expert system devices wherein the output comprises processed diagnostic raw data the interpretation of which does not require a specialized clinician.

Further preferred embodiments of the invention are derived from the dependent claims together with the following description, whereby the patent claims of a certain category may be formed by dependent claims of a different category, and features of the different examples may be combined to new examples. It is to be understood that the definitions and explanations of the terms made above and below apply accordingly for all embodiments described in this specification and the accompanying claims. In the following, particular embodiments of the method of the present invention are specified further.

Beneficially, by implementing the method according to the present invention, sensitivity and specificity of prediction accuracy can be higher than about 80%, preferably higher than about 85%, more preferably higher than about 90%. Thus, the method of the present invention improves decision making of clinicians prior to the application of an expensive and cumbersome therapeutic measure such as cardiac therapy. Making the right decision, i.e. applying the therapy only if it is effective, will certainly also be beneficial for the individual patients and, in light of the cost consequences, for the public health system as such.

It has been advantageously found in the studies underlying the present invention that analysing the amount of a combination of the biomarkers, wherein the Growth factor is preferably selected from VEGF and/or Erythropoietin and optionally from FGF, the Lymphocyte adapter protein is preferably selected from SH2B3, the Glycoprotein is preferably selected from Vitronectin and optionally from GCSF, the brain natriuretic peptide is preferably selected from NT-proBNP, the circulating endothelial progenitor cells (EPC) are preferably selected from CD45$^+$, CD117$^+$, CD184$^+$, CD133$^+$, CD146$^+$ cells, the circulating endothelial cells (CEC) are preferably selected from CD133$^+$, CD146$^+$, CD105$^+$, CD34$^+$ cells, circulating thrombocytes, circulating mononuclear cells and subpopulations, and receptor/ligand expression on MNC subpopulations is preferably selected from CD184$^+$ and/or CD309$^+$ cells, cell adhesion molecules (CAM) and/or integrin receptors, in a sample taken prior to cardiac therapy from a subject in need of said cardiac therapy, e.g. a subject suffering from heart failure, allows for predicting whether that subject will benefit from the therapy in that the cardiac regeneration or cardiovascular repair is improved after therapy. The techniques for measuring the amounts of the individual biomarkers are all well known in the art.

By using machine learning (ML), the method is preferably further assisted since no individual comparisons must be carried out. Furthermore, the machine learning beneficially serves to balance and weighting the parameters such that reliability of the prediction can be further improved. Thus, an advantageous method of the present invention is preferably assisted by machine learning to facilitate and improve prediction accuracy. In accordance with the present invention, the term "machine learning" relates to the study and construction of algorithms that can learn from and make predictions on data—the algorithms hereby overcome strictly static program instructions by making data-driven predictions or decisions through building a model from sample inputs.

In a preferred embodiment of the inventive method, such method uses further biomarkers, wherein the further biomarkers are preferably selected from the group of Cytokine, Interleukin, Interferon, Insulin-like-growth-factor-binding protein, Insulin-like Growth factor, Chemokine protein and/or Multi-protein E3 ubiquitin ligase complex.

In accordance with such a method, the Cytokine is preferably selected from TNF, the Interleukin is preferably selected from IL-6, IL-8 and/or IL-10, the Interferon is preferably selected from Human interferon gamma-induced protein 10, the Insulin-like-growth-factor-binding protein is preferably selected from Insulin-like-growth-factor-binding protein-2 and/or Insulin-like-growth-factor-binding protein-3, the Insulin-like growth factor is preferably selected from IGF2, the Chemokine protein is preferably selected from SDF-1 and/or the Multi-protein E3 ubiquitin ligase complex is preferably selected from SCF.

In another preferred embodiment, the method is used for preoperative prediction of response to stem cell therapy and/or induction of angiogenesis response and/or tissue repair in the context of cardiovascular disease including myocardial infarction, stroke and peripheral ischemic vascular disease, heart disease and/or ischemic preconditioning. Such a therapy may include a treatment to use a cardiovascular implant or stent, a ventricular assist device (VAD), a pacemaker and/or an occluder or appropriate closure device. Also, such a therapy may include treatment of diabetes mellitus, tumor diseases, coeliakie, rheumatic diseases, infectious diseases, sepsis and/or hypertension. In particular, the method is used for preoperative prediction of improvement of left ventricular heart function, e.g. following deterioration of left ventricular ejection fraction (LVEF) after acute myocardial ST-segment elevations infarction (STEMI) and coronary artery 3-vessel disease sequentially treated by acute percutaneous coronary intervention (PCI) and secondary coronary artery bypass graft (CABG) revascularization.

In yet another preferred embodiment, the method for prediction of response to cardiac regeneration, in particular to stem cell therapy and/or induction of angiogenesis response and/or tissue repair in the context of cardiovascular disease uses a sample taken from a subject suffering from heart disease and/or arteriosclerosis. Such a sample may particularly taken from a subject suffering from angina, acute myocardial injury, cellular necrosis, myocardium hypertrophy, heart failure, preferably ischemic heart failure, non-ischemic heart failure, myocarditis, atrial fibrillation, ventricular fibrillation and/or arteriosclerosis.

According to a preferred embodiment, the method comprises profiling of the results of the comparison of at least two, three, four, five, six or more time points. Advantageously, such time points comprise a sample taken preoperative and about 1, 3, 10, 90, and/or 180 days post operation. By analysing the samples of at least two, three, four, five, six or more time points, specificity of prediction accuracy can be beneficially increased to more than 90%, preferably to more than 91%, 92%, 93%, 94%, 95% and even more.

A further embodiment of the beneficial method comprises the use of clinical diagnostic parameters. In particular, such parameters are selected from colony forming unit (CFU) Hill assay, Matrigel Plug assay, weight, and/or left ventricular end-systolic volume (LVESV).

According to a next preferred embodiment, the method is used for profiling of angiogenesis response.

Yet another preferred embodiment includes for the advantageous method to further comprise analysing an RNA and/or DNA and/or mRNA sequence and/or functional RNA such as microRNA and/or non-coding RNA and/or SNP comprising a diagnostic signature. Within the context of the invention, such a signature analysis of an RNA and/or DNA and/or SNP may be performed and/or supported by machine learning and/or pathway analysis. In the context of the present invention, pathway analysis is used to identify related RNA and/or DNA and/or SNP within a pathway or building pathway de novo from the RNA, DNA and/or SNP of interest.

Also, according to a further preferred embodiment, the advantageous method may comprise analysis of pharmacokinetic and pharmacogenetic data employing RNA and/or DNA sequencing analysis and/or network pathway analysis. Such pharmacokinetic data may be in particular obtained from subjects given medications from the group selected from a Statin, acetylsalicylic acid (ASS), a β-blocker, an angiotensin-converting-enzyme (ACE) inhibitor, an angiotensin II (ATII) receptor antagonist, an Aldosterone antagonist, a diuretic agent, a Ca-antagonist, an anti-Arrhythmic agent, Digitalis, Marcumar, and/or Nitrate.

A next preferred embodiment may additionally use analysis of phenotype of the subject, such as analysis of body weight.

According to an even further preferred embodiment, the method for prediction of cardiovascular repair comprises stem cell therapy to use transplantation of CD133 positive stem cells. Such a stem cell therapy may be optionally combined with CABG revascularization, used for induction of cardiac regeneration, and/or PCI. Though, a particularly preferred embodiment includes that cardiac stem cell therapy further comprises coronary artery bypass graft surgery.

Advantageously, cardiac regeneration and/or functional improvement of the heart after cardiac stem cell therapy are accompanied by an increase of LVEF of at least 5%.

The aforementioned inventive method is not restricted to be applied for human subjects only, but may also include animals. However, it is preferred for the method to be applied to human subject/s. In accordance with the invention, a sample of such a subject may be derived from blood, in particular peripheral blood, and/or a serum and/or a plasma sample and/or a tissue biopsy sample and/or a sample of circulating (stem) cells such as endothelial progenitor cells (EPC).

As depicted above, the present invention also pertains to a combination of biomarkers selected from the group of Growth factor, Lymphocyte adapter protein, Glycoprotein, brain natriuretic peptide, circulating endothelial progenitor cells, circulating endothelial cells, circulating thrombocytes, circulating mononuclear cells and subpopulations thereof, and receptor/ligand expression on MNC subpopulations for use in a method for prediction of response to cardiovascular regeneration. Advantageously, the method is an ex vivo or in vitro method.

Preferably, the biomarkers are used in a method for prediction of response to cardiovascular regeneration, the method comprising
  (i) determining in a sample of a subject the amount of each of the biomarkers,
  (ii) comparing the determined amounts to a baseline value and/or a reference,
  (iii) predicting, based on the results of the comparison, whether a response to cardiovascular repair in the subject is to be expected, not expected or is ambivalent.

According to a preferred embodiment the Growth factor is preferably selected from VEGF and/or Erythropoietin and optionally from FGF, the Lymphocyte adapter protein is preferably selected from SH2B3, the Glycoprotein is preferably selected from Vitronectin and optionally from GCSF, and the brain natriuretic peptide is preferably selected from NT-proBNP.

In addition, the combination of biomarkers preferably comprises further biomarkers selected from the group of Cytokine, Interleukin, Interferon, Insulin-like-growth-factor-binding protein, Chemokine protein and/or Multi-protein E3 ubiquitin ligase complex. Even more preferably the Cytokine is selected from TNF, the Interleukin is selected from IL-6, IL-8 and/or IL-10, the Interferon is selected from Human interferon gamma-induced protein 10, the Insulin-like-growth-factor-binding protein is selected from Insulin-like-growth-factor-binding protein-2 and/or Insulin-like-growth-factor-binding protein-3, the Insulin-like growth factor is preferably selected from IGF2, the Chemokine protein is selected from SDF-1, and/or the Multi-protein E3 ubiquitin ligase complex is selected from SCF.

According to a preferred embodiment of the present invention, a combination of the above biomarkers are used in a method for prediction of response to cardiovascular regeneration, wherein the method further comprises analysis of clinical diagnostic data, and/or RNA and/or mRNA and/or functional RNA such as microRNA and/or non-coding RNA and/or SNP, and/or analysis of pharmacokinetic data, and/or analysis of phenotyping, e.g. body weight.

Yet more preferably, an advantageous method and/or an advantageous combination of the above biomarkers is/are used for preoperative prediction of response to stem cell therapy and wherein the stem cell therapy is accompanied by CABG.

The term "stem cell therapy" as used herein refers to all therapeutic approaches which comprise the transplantation of exogenous cardiomyocytes into the heart of a subject to be treated. Such cardiomyocytes may be generated by reprogramming non-cardiomyocyte progenitor cells into cardiomyocytes. Cells to be reprogrammed may be embryonic stem cells, induced pluripotent stem cells, multipotent cardiac progenitor cells, skeletal myoblasts or bone marrow derived stem cells. Moreover, mature cardiomyocytes may also be used, in particular, if stimulated to reenter into mitotic cell cycling. More preferably, the cardiac stem cell therapy according to the present invention comprises transplantation of CD133-positive cells, most preferably, CD133-positive bone marrow mononuclear cells. The cells may be transplanted as isolated single cells or in a preformed arrangement such as a tissue block formed by tissue engineering processes. Preferably, the cells are transplanted in accordance with the present invention by intra-myocardial injection. Moreover, the term cardiac stem cell therapy may also encompass additional therapeutic measures such as drug treatments accompanying the transplantation process or other therapeutic measures such as surgery. Preferably, the cardiac stem cell therapy in accordance with the present invention further comprises coronary artery bypass graft surgery as described in the accompanying examples below.

The term "functional improvement of the heart" as used herein refers to a significant increase in the LVEF of the heart observed when comparing said LVEF before and after treatment of the subject. Preferably, a significant increase is an increase of 5% or more of LVEF observed after treatment. An increase of less than 5% is deemed to be insignificant. Further parameters which may be considered in addition for finding a functional improvement are a more than 10% decrease in perfusion defect size, a more than 10% decrease in left ventricle end systolic volume (LVESV) as quantified by MIBI SPECT and a more than 10% increase in peak systolic velocity measured by transthoracic echocardiogram.

Heart failure as used herein refers to any functional impairment of the heart including left-sided failures, right-sided failures or biventricular failures. Typically, the term heart failure as referred to herein is left-sided failure that results in reduced ejection fractions, e.g. a significantly reduced LVEF. Further symptoms of heart failure are well known to the clinician. Heart failure as referred to herein encompasses acute and chronic forms of heart failure and any stage of severity, e.g. for left-sided failures all stages according to the New York Heart Association (NYHA) classification system, NYHA I to IV.

The term "vascular endothelial growth factor (VEGF)" as used herein refers to soluble polypeptide growth factor which stimulates angiogenesis, vasculogenesis and vascular permeability. It is produced by various cell types. There are five different VEGF polypeptides, VEGF-A, placenta growth factor (PGF), VEGF-B, VEGF-C, and VEGF-D. As used herein, preferably, VEGF-A is envisaged. There are various isoforms resulting from alternative splicing known for VEGF-A. The most prominent ones are $VEGF_{121}$, $VEGF_{121}b$, $VEGF_{145}$, $VEGF_{165}$, $VEGF_{165}b$, $VEGF_{189}$, and $VEGF_{206}$.

Preferably, VEGF refers to human VEGF-A as described in Tischer 1991, J. Biol. Chem. 266 (18): 11947-11954 (disclosed is the longest isoform for VEGF-A). For amino acid sequences, see, e.g., also Genbank accession numbers NP_001020537.2, GI: 76781480 (Genbank is available from the NCBI, USA under www.ncbi.nlm.nih.gov/entrez). The term also encompasses variants of the aforementioned human VEGF polypeptides. Such variants have at least the same essential biological and immunological properties as the aforementioned VEGF polypeptide. In particular, they share the same essential biological and immunological properties if they are detectable by the same specific assays referred to in this specification, e.g. by ELISA assays using polyclonal or monoclonal antibodies specifically recognizing the said VEGF polypeptides. Moreover, it is to be understood that a variant as referred to in accordance with the present invention shall have an amino acid sequence which differs due to at least one amino acid substitution, deletion and/or addition wherein the amino acid sequence of the variant is still, preferably, at least 50%, 60%, 70%, 80%, 85%, 90%, 92%, 95%, 97%, 98%, or 99% identical with the amino sequence of the specific VEGF polypeptide, preferably over the entire length of the human VEGF, respectively. The degree of identity between two amino acid sequences can be determined by algorithms well known in the art. Preferably, the degree of identity is to be determined by comparing two optimally aligned sequences over a comparison window, where the fragment of amino acid sequence in the comparison window may comprise additions or deletions (e.g., gaps or overhangs) as compared to the reference sequence (which does not comprise additions or deletions) for optimal alignment. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm disclosed by Smith 1981, Add. APL. Math. 2:482, by the homology alignment algorithm of Needleman 1970, J. Mol. Biol. 48:443, by the search for similarity method of Pearson 1988, Proc. Natl. Acad Sci. (USA) 85: 2444, by computerized implementations of these algorithms (GAP, BESTFIT, BLAST, FAST, PASTA, and TFASTA in the Wisconsin Genetics Software Package, Genetics Computer Group (GCG), 575 Science Dr., Madison, Wis.), or by visual inspection. Given that two sequences have been identified for comparison, GAP and BESTFIT are preferably employed to determine their optimal alignment and, thus, the degree of identity. Preferably, the default values of 5.00 for gap weight and 0.30 for gap weight length are used. Variants referred to above may be allelic variants or any other species specific homologs, paralogs, or orthologs. Variants referred to above may be allelic variants or any other species specific homologs, paralogs, or orthologs. Moreover, the variants referred to herein include fragments or subunits of the specific VEGF polypeptides or the aforementioned types of variants as long as these fragments have the essential immunological and biological properties as referred to above. Such fragments may be, e.g., degradation products of the VEGF polypeptides. Variants are deemed to share the same essential biological and immunological properties if they are detectable by the same specific assays referred to in this specification, e.g., by ELISA assays using polyclonal or monoclonal antibodies specifically recognizing the said VEGF polypeptides. A preferred assay is described in the accompanying examples. Further included are variants which differ due to posttranslational modifications such as phosphorylation or myristylation. VEGF may be detected in bound or free form or as total VEGF amount in a sample.

The term "Fibroblast growth factor (FGF)" as used herein refers to a family of growth factors, with members involved in angiogenesis, wound healing, embryonic development and various endocrine signaling pathways.

The term "Erythropoietin (EPO)" as used herein refers to a soluble polypeptide being a cytokine. It is produced by kidney cells, typically, under hypoxic conditions.

Preferably, EPO refers to human IL-6 as described, e.g. in Yanagawa 1984, J. Biol. Chem. 259(5): 2707-2710. More preferably, human IL-6 has an amino acid sequence as shown in Genbank accession number p01588.1, GI: 119526. The term also encompasses variants of the aforementioned human EPO polypeptides. Such variants have at least the same essential biological and immunological properties as the aforementioned EPO polypeptide. In particular, they share the same essential biological and immunological properties if they are detectable by the same specific assays referred to in this specification, e.g., by ELISA assays using polyclonal or monoclonal antibodies specifically recognizing the said EPO polypeptides. Moreover, it is to be understood that a variant as referred to in accordance with the present invention may have an amino acid sequence which differs due to at least one amino acid substitution, deletion and/or addition wherein the amino acid sequence of the variant is still, preferably, at least 50%, 60%, 70%, 80%, 85%, 90%, 92%, 95%, 97%, 98%, or 99% identical with the amino sequence of the specific IL-6. Variants may be allelic variants, splice variants or any other species specific homologs, paralogs, or orthologs. Moreover, the variants referred to herein include fragments of the specific EPO or the aforementioned types of variants as long as these fragments have the essential immunological and biological properties as referred to above. Such fragments may be, e.g., degradation products of EPO. Variants are deemed to share the same essential biological and immunological properties if they are detectable by the same specific assays referred to in this specification, e.g., by ELISA assays using polyclonal or monoclonal antibodies specifically recognizing the said EPO polypeptides. A preferred assay is described in the accompanying Examples. Further included are variants which differ due to posttranslational modifications such as phosphorylation or myristylation.

The term "SH2B adapter protein 3 (SH2B3)" as used herein refers to lymphocyte adapter protein (LNK). SH2B3 is a protein that in humans is encoded by the SH2B3 gene on chromosome 12. It is ubiquitously expressed in many tissues and cell types (Li Y, He X, Schembri-King J, Jakes S, Hayashi J, May 2000. Journal of Immunology. 164(10): 5199-206).

The term "Vitronectin (VTN)" as used herein refers to a glycoprotein of the hemopexin family which is abundantly found in serum, the extracellular matrix and bone (Boron, Walter F. and Boulpaep, Emile L. "Medical Physiology". Saunders, 2012, p. 1097). In humans it is encoded by the VTN gene. Vitronectin binds to integrin alpha-V beta-3 and thus promotes cell adhesion and spreading. It also inhibits the membrane-damaging effect of the terminal cytolytic complement pathway, and binds to several serpins (serine protease inhibitors). It is a secreted protein and exists in either a single chain form or a clipped, two chain form held together by a disulfide bond. Vitronectin has been speculated to be involved in hemostasis and tumor malignancy.

The term "granulocyte-colony stimulating factor (G-CSF or GCSF)", also known as colony-stimulating factor 3 (CSF 3), is a glycoprotein that stimulates the bone marrow to produce granulocytes and stem cells and release them into the bloodstream. Functionally, it is a cytokine and a hormone, a type of colony-stimulation factor, and is produced by a number of different tissues. G-CSF also stimulates the survival, proliferation, differentiation, and function of neutrophil precursors and mature neutrophils.

The term "Brain natriuretic peptide or B-type natriuretic peptide (BNP)", also named ventricular natriuretic peptide or natriuretic peptide B is a 32-amino acid polypeptide secreted by the ventricles of the heart in response to excessive stretching of heart muscle cells (cardiomyocytes). The release of BNP is modulated by calcium ions. BNP is named as such because it was originally identified in extracts of porcine brain, although in humans it is produced mainly in the cardiac ventricles. BNP is secreted attached to a 76-amino acid N-terminal fragment in the prohormone called NT-proBNP. Once released, BNP binds to and activates the atrial natriuretic factor receptors (NPRA), and to a lesser extent NPRB in a fashion similar to atrial natriuretic peptide (ANP) but with 10-fold lower affinity. The biological half-life of BNP, however, is twice as long as that of ANP, and that of NT-proBNP is even longer, making these peptides better targets than ANP for diagnostic blood testing.

The term "Interleukin-6 (IL-6)" as used herein refers to a soluble polypeptide being a pro-inflammatory cytokine and anti-inflammatory myokine. It is produced by T-cells and macrophages.

Preferably, IL-6 refers to human IL-6 as described, e.g., in Wong 1988, Behring Inst. Mitt 83: 40-47. More preferably, human Il-6 has an amino acid sequence as shown in Genbank accession number p05231.1, GI: 124347. The term also encompasses variants of the aforementioned human IL-6 polypeptides. Such variants have at least the same essential biological and immunological properties as the aforementioned IL-6 polypeptide. In particular, they share the same essential biological and immunological properties if they are detectable by the same specific assays referred to in this specification, e.g., by ELISA assays using polyclonal or monoclonal antibodies specifically recognizing the said IL-6 polypeptides. Moreover, it is to be understood that a variant as referred to in accordance with the present invention may have an amino acid sequence which differs due to at least one amino acid substitution, deletion and/or addition wherein the amino acid sequence of the variant is still, preferably, at least 50%, 60%, 70%, 80%, 85%, 90%, 92%, 95%, 97%, 98%, or 99% identical with the amino sequence of the specific IL-6. Variants may be allelic variants, splice variants or any other species specific homologs, paralogs, or orthologs. Moreover, the variants referred to herein include fragments of the specific IL-6 or the aforementioned types of variants as long as these fragments have the essential immunological and biological properties as referred to above. Such fragments may be, e.g., degradation products of IL-6. Variants are deemed to share the same essential biological and immunological properties if they are detectable by the same specific assays referred to in this specification, e.g., by ELISA assays using polyclonal or monoclonal antibodies specifically recognizing the said IL-6 polypeptides. A preferred assay is described in the accompanying Examples. Further included are variants which differ due to posttranslational modifications such as phosphorylation or myristylation.

The term "Interferon gamma-induced protein 10 (IP-10)" as used herein refers to a soluble polypeptide being a cytokine belonging to the CXC chemokine family. It is produced by monocytes, endothelial cells and fibroblasts.

Preferably, IP-10 refers to human IP-10 as described, e.g. in Booth 2002, Biochemistry 41(33): 10418-10425. More preferably, human IP-10 has an amino acid sequence as shown in Genbank accession number p02778.2, GI: 21542456. The term also encompasses variants of the aforementioned human IP-10 polypeptides. Such variants have at least the same essential biological and immunological properties as the aforementioned IP-10 polypeptide. In particular, they share the same essential biological and immunological properties if they are detectable by the same specific assays referred to in this specification, e.g., by ELISA assays using polyclonal or monoclonal antibodies specifically recognizing the said IP-10 polypeptides. Moreover, it is to be understood that a variant as referred to in accordance with the present invention may have an amino acid sequence which differs due to at least one amino acid substitution, deletion and/or addition, wherein the amino acid sequence of the variant is still, preferably, at least 50%, 60%, 70%, 80%, 85%, 90%, 92%, 95%, 97%, 98%, or 99% identical with the amino sequence of the specific IP-10. Variants may be allelic variants, splice variants or any other species specific homologs, paralogs, or orthologs. Moreover, the variants referred to herein include fragments of the specific IP-10 or the aforementioned types of variants as long as these fragments have the essential immunological and biological properties as referred to above. Such fragments may be, e.g. degradation products of IP-10. Variants are deemed to share the same essential biological and immunological properties if they are detectable by the same specific assays referred to in this specification, e.g. by ELISA assays using polyclonal or monoclonal antibodies specifically recognizing the said IP-10 polypeptides. A preferred assay is described in the accompanying examples. Further included are variants which differ due to posttranslational modifications such as phosphorylation or myristylation.

The term "Insulin-like growth factor-binding protein 3 (IGFBP-3)" as used herein refers to a soluble polypeptide being a growth factor of the family of insulin-like growth factors. It is produced by various cells.

Preferably, IGFBP-3 refers to human IGFBP-3 as described, e.g. in Thweatt 1993, DNA Seq 4(1): 43-46. More preferably, human IL-6 has an amino acid sequence as shown in Genbank accession number p17936.1, GI: 146327827. The term also encompasses variants of the aforementioned human IGFBP-3 polypeptides. Such variants have at least the same essential biological and immunological properties as the aforementioned IGFBP-3 polypeptide. In particular, they share the same essential biological and immunological properties if they are detectable by the same specific assays referred to in this specification, e.g. by ELISA assays using polyclonal or monoclonal antibodies specifically recognizing the said IGFBP-3 polypeptides. Moreover, it is to be understood that a variant as referred to in accordance with the present invention may have an amino acid sequence which differs due to at least one amino acid substitution, deletion and/or addition wherein the amino acid sequence of the variant is still, preferably, at least 50%, 60%, 70%, 80%, 85%, 90%, 92%, 95%, 97%, 98%, or 99% identical with the amino sequence of the specific IGFBP-3. Variants may be allelic variants, splice variants or any other species specific homologs, paralogs, or orthologs. Moreover, the variants referred to herein include fragments of the specific IGFBP-3 or the aforementioned types of variants as long as these fragments have the essential immunological and biological properties as referred to above. Such fragments may be, e.g., degradation products of IGFBP-3. Variants are deemed to share the same essential biological and immunological properties if they are detectable by the same specific assays referred to in this specification, e.g. by ELISA assays using polyclonal or monoclonal antibodies specifically recognizing the said IGFBP-3 polypeptides. A preferred assay is described in the accompanying Examples. Further included are variants which differ due to posttranslational modifications such as phosphorylation or myristoylation.

The term "insulin-like growth factor (IGF2)" as used herein refers to one of three protein hormones that share structural similarity to insulin. IFG2 is believed to be secreted by the liver and to circulate in the blood. It has growth-regulating, insulin-like and mitogenic activities. The growth factor has a major, but not absolute, dependence on somatotropin. It is believed to be a major fetal growth factor.

The term "stromal cell-derived factor 1 (SDF1)", also known as C-X-C motif chemokine 12 (CXCL12), is a chemokine protein that in humans is encoded by the CXCL12 gene on chromosome 10. It is ubiquitously expressed in many tissues and cell types. Stromal cell-derived factors 1-alpha and 1-beta are small cytokines that belong to the chemokine family, members of which activate leukocytes and are often induced by pro-inflammatory stimuli such as lipopolysaccharide, TNF, or IL1. The chemokines are characterized by the presence of four conserved cysteines that form two disulfide bonds.

The term "skp, cullin, f-box containing complex (or SCF)" refers to a multi-protein E3 ubiquitin ligase complex catalyzing the ubiquitination of proteins destined for proteasomal degradation. It has important roles in the ubiquitination of proteins involved in the cell cycle and also marks various other cellular proteins for destruction.

Determining the amount of a biomarker may, preferably, comprise the steps of (a) contacting the biomarker with a specific ligand, (b) (optionally) removing non-bound ligand, (c) measuring the amount of bound ligand. The bound ligand will generate an intensity signal. Binding according to the present invention includes both covalent and non-covalent binding. A ligand according to the present invention can be any compound, e.g., a peptide, polypeptide, nucleic acid, or small molecule, binding to the peptide or polypeptide or protein or nucleic acid or cell described herein. Preferred ligands include antibodies, nucleic acids, peptides or polypeptides such as receptors or binding partners for the peptide or polypeptide and fragments thereof comprising the binding domains for the peptides, and aptamers, e.g. nucleic acid or peptide aptamers. Methods to prepare such ligands are well-known in the art. For example, identification and production of suitable antibodies or aptamers is also offered by commercial suppliers. The person skilled in the art is familiar with methods to develop derivatives of such ligands with higher affinity or specificity. For example, random mutations can be introduced into the nucleic acids, peptides or polypeptides. These derivatives can then be tested for binding according to screening procedures known in the art, e.g. phage display. Antibodies as referred to herein include both polyclonal and monoclonal antibodies, as well as fragments thereof, such as Fv, Fab and F(ab)$_2$ fragments that are capable of binding antigen or hapten. The present invention also includes single chain antibodies and humanized hybrid antibodies wherein amino acid sequences of a non-human donor antibody exhibiting a desired antigen-specificity are combined with sequences of a human acceptor antibody. The donor sequences will usually include at least the antigen-binding amino acid residues of the donor but may comprise other structurally and/or functionally relevant amino acid residues of the donor antibody as well. Such hybrids can be prepared by several methods well known in the art. Preferably, the ligand or agent binds specifically to the peptide or polypeptide. Specific binding according to the present invention means that the ligand or agent should not bind substantially to ("cross-react" with) another peptide, polypeptide or substance present in the sample to be analysed. Preferably, the specifically bound peptide or polypeptide should be bound with at least 3 times higher, more preferably at least 10 times higher and even more preferably at least 50 times higher affinity than any other relevant peptide or polypeptide. Non-specific binding may be tolerable, if it can still be distinguished and measured unequivocally, e.g. according to its size on a Western Blot, or by its relatively higher abundance in the sample. Binding of the ligand can be measured by any method known in the art. Preferably, said method is semi-quantitative or quantitative. Further suitable techniques for the determination of a biomarker are described in the following.

First, binding of a ligand may be measured directly, e.g. by NMR or surface plasmon resonance. Second, if the ligand also serves as a substrate of an enzymatic activity of the biomarker of interest, an enzymatic reaction product may be measured (e.g. the amount of a protease can be measured by measuring the amount of cleaved substrate, e.g. on a Western Blot). Alternatively, the ligand may exhibit enzymatic properties itself and the "ligand/peptide or polypeptide" complex or the ligand which was bound by the biomarker, respectively, may be contacted with a suitable substrate allowing detection by the generation of an intensity signal. For measurement of enzymatic reaction products, preferably the amount of substrate is saturating. The substrate may also be labelled with a detectable label prior to the reaction. Preferably, the sample is contacted with the substrate for an adequate period of time. An adequate period of time refers to the time necessary for a detectable, preferably measurable, amount of product to be produced. Instead of measuring the amount of product, the time necessary for appearance of a given (e.g. detectable) amount of product can be measured. Third, the ligand may be coupled covalently or non-covalently to a label allowing detection and measurement of the ligand. Labelling may be done by direct or indirect methods. Direct labelling involves coupling of the label directly (covalently or non-covalently) to the ligand. Indirect labelling involves binding (covalently or non-covalently) of a secondary ligand to the first ligand. The secondary ligand should specifically bind to the first ligand. Said secondary ligand may be coupled with a suitable label and/or be the target (receptor) of tertiary ligand binding to the secondary ligand. The use of secondary, tertiary or even higher order ligands is often used to increase the signal. Suitable secondary and higher order ligands may include antibodies, secondary antibodies, and the well-known streptavidin-biotin system. The ligand or substrate may also be "tagged" with one or more tags as known in the art. Such tags may then be targets for higher order ligands. Suitable tags include biotin, digoxygenin, His-Tag, Glutathion-S-Transferase, FLAG, GFP, myc-tag, influenza A virus haemagglutinin (HA), maltose binding protein, and the like. In the case of a peptide or polypeptide, the tag is preferably at the N-terminus and/or C-terminus. Suitable labels are any labels detectable by an appropriate detection method. Typical labels include gold particles, latex beads, acridin ester, luminol, ruthenium, enzymatically active labels, radioactive labels, magnetic labels ("e.g. magnetic beads", including paramagnetic and superparamagnetic labels), and fluorescent labels. Enzymatically active labels include e.g. horseradish peroxidase, alkaline phosphatase, beta-Galactosidase, Luciferase, and derivatives thereof. Suitable substrates for detection include di-amino-benzidine (DAB), 3,3'-5,5'-tetramethylbenzidine, NBT-BCIP (4-nitro blue tetrazolium chloride and 5-bromo-4-chloro-3-indolyl-phosphate. A suitable enzyme-substrate combination may result in a coloured reaction product, fluorescence or chemoluminescence, which can be measured according to methods known in the art (e.g. using a light-sensitive film or a suitable camera system). As for measuring the enzymatic reaction, the criteria given above apply analogously. Typical fluorescent labels include fluorescent proteins (such as GFP and its derivatives), Cy3, Cy5, Texas Red, Fluorescein, and the Alexa dyes. Further fluorescent labels are available e.g. from Molecular Probes (Oregon). Also the use of quantum dots as fluorescent labels is contemplated. Typical radioactive labels include $^{35}$S, $^{125}$I, $^{32}$P, $^{33}$P and the like. A radioactive label can be detected by any method known and appropriate, e.g. a light-sensitive film or a phosphor imager.

The amount of a biomarker may be, also preferably, determined as follows: (a) contacting a solid support comprising a ligand for the biomarker as specified above with a sample comprising the biomarker and (b) measuring the amount of biomarker which is bound to the support. The ligand, preferably chosen from the group consisting of nucleic acids, peptides, polypeptides, antibodies and aptamers, is preferably present on a solid support in immobilized form. Materials for manufacturing solid supports are well known in the art and include, inter alia, commercially available column materials, polystyrene beads, latex beads, magnetic beads, colloid metal particles, glass and/or silicon chips and surfaces, nitrocellulose strips, membranes, sheets, duracytes, wells and walls of reaction trays, plastic tubes etc. The ligand or agent may be bound to many different carriers. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention. Suitable methods for fixing/immobilizing said ligand/s are well known and include, but are not limited to ionic, hydrophobic or covalent interactions and the like.

Suitable measurement methods according to the present invention also include FACS analysis, radioimmunoassay (RIA), enzyme-linked immunosorbent assay (ELISA), sandwich enzyme immune tests, electrochemiluminescence sandwich immunoassays (ECLIA), dissociation-enhanced lanthanide fluoro immuno assay (DELFIA), scintillation proximity assay (SPA) or solid phase immune tests. Further methods known in the art (such as gel electrophoresis, 2D gel electrophoresis, SDS polyacrylamid gel electrophoresis (SDS-PAGE), Western Blotting and mass spectrometry (MS) can be used alone or in combination with labelling or other detection methods as described above.

In order to carry out the method of the present invention, a kit is provided which is adapted for carrying out the inventive method, wherein the kit according to the present invention comprises detection agents for determining in a sample of said subject the amount of at least one of the above biomarkers. Such a kit advantageously allows for a straight forward conduction of the inventive method and/or measurement and/or determination of the biomarker/s according to the present invention.

The term "kit" as used herein refers to a collection of the aforementioned components, preferably, the components being provided separately or within a single container. The kit may also comprise instructions for carrying out the method of the present invention. These instructions may be in the form of a manual or may be provided by a computer program code which is capable of carrying out the comparisons referred to in the methods of the present invention and to establish a diagnosis accordingly when implemented on a computer or a data processing device. The computer program code may be provided on a data storage medium or device such as a storage medium (e.g. a Compact Disc, USB drives or external hard disks) or directly on a computer or data processing device. Moreover, the kit may, preferably, comprise standards for reference amounts as described elsewhere herein in detail.

Further characteristics of the present invention are derived from the examples in combination with the claims and the figures. Single features may be, in a particular embodiment, realised in combination with other features and do not limit the scope of protection of the present invention. The following description of the examples according to the invention may relate to the figures, whereby FIG. 1 depicts SH2B3 expression analysis in peripheral blood of responder and non-responder. Whole blood samples were obtained from 21 patients before coronary artery bypass graft (CABG) revascularization. Relative expression of SH2B3 (a) and corresponding $\Delta CT$ values (b) were calculated using the $2^{-\Delta\Delta CT}$ method. All values are presented as mean±SEM and normalized to GAPDH and POLR2A. n=13 (responder); n=8 (non-responder). $\Delta CT$ values: p=0.073.

Figure 2:
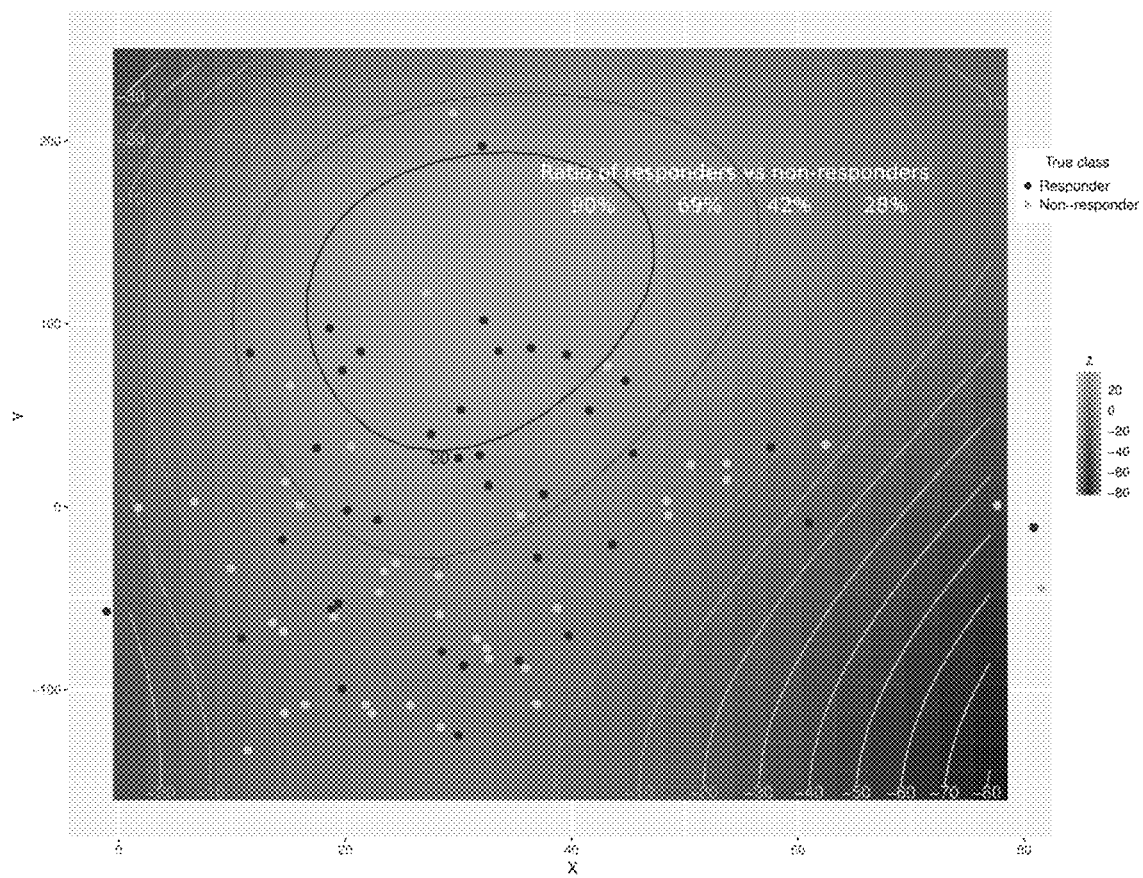

FIG. 2 shows a three-dimensional t-distributed stochastic neighbor embedding (t-SNE) calculation that refers to unsupervised ML. This independent methodology reduces the dimensionality of a given parameter set, e.g. biomarker profile, and thus calculates the variables x, y and z that likewise refer to newly calculated features, which are used to classify the patients into distinct groups. The model was subsequently fitted by a polynomial (n3) equation to visualize the z-axis as a geographic profile. The respective colors for the responder (black dot) and non-responder (grey dot) patients have been added afterwards. The classified groups have been roughly summarized by a black and a grey dashed line. Results are obtained after 3000 iterations. The calculation of the ratio between responder and non-responder is indicated for each circle. It is more likely for the non-responder group to be located at smaller z-values (z<20, ratio<42%). The responders tend to be enriched within the light grey areas (z>20) including a ratio of greater than 69%.

Figure 3:
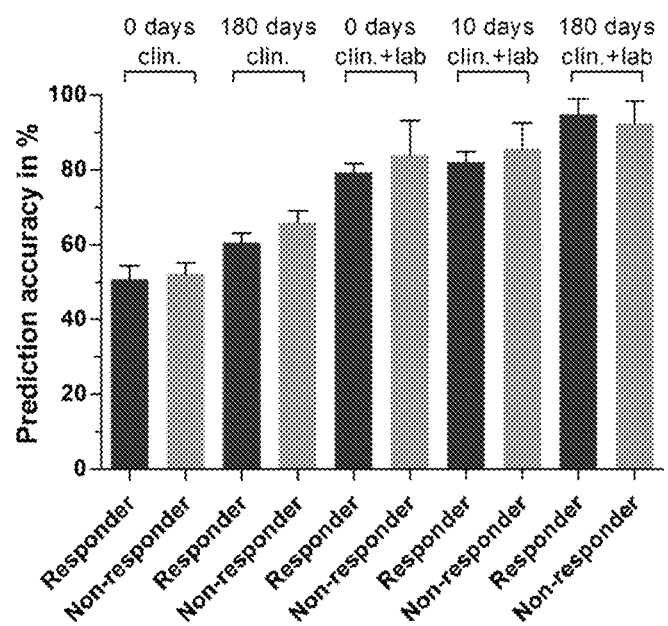

FIG. 3 depicts ML prediction results for pre- and post-operative time points (0 days to 180 days) of the clinical and clinical & laboratory dataset to distinguish between responder and non-responder. The graph shows the true positive prediction rate of five independent feature selected ML models (AdaBoost for feature selection and Random Forest (RF) for final prediction). The error bars indicate the respective accuracy standard deviation for the constructed models that have been obtained after 100 iterations. The 100 model iterations are significantly different according to one-way ANOVA (p<0.001).

Figure 4:
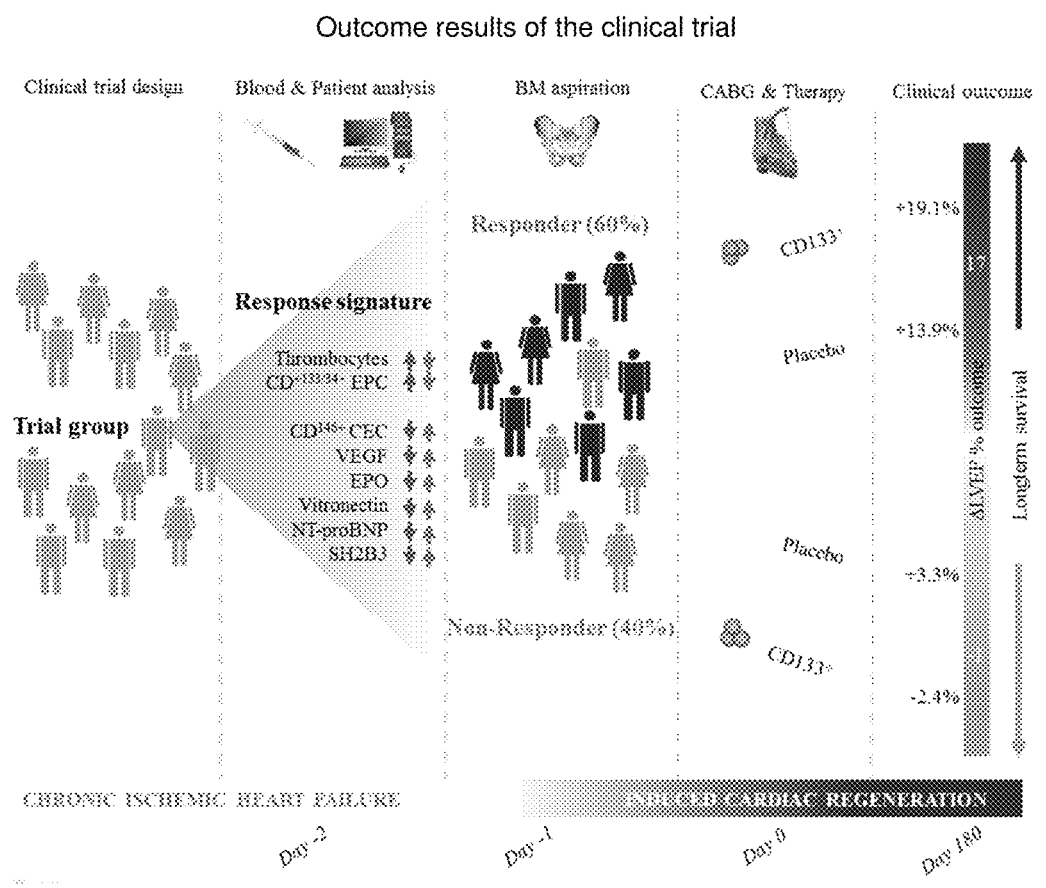

FIG. 4 shows the Outcome results of the PERFECT trial. Diagnostic discrimination of primary endpoint outcome responders in the PERFECT trial by distinctive preoperative peripheral blood parameters signature linked to bone marrow/blood CD133$^+$, CD34$^+$, CD117$^+$, EPC and angiogenesis response.

EXAMPLES

The following examples shall merely illustrate the invention. They shall, whatsoever, not be construed as limiting the scope thereof.

Example 1

Clinical Study Design and Evaluation

Induction of cardiac regeneration in patients with heart failure after myocardial infarction and ischemic cardiomyopathy has been targeted using multiple approaches including stem cell therapy. Thereby, lack of efficacy and lack of response predictability have been the main obstacles for treatment standardization and success.

A clinical trial was performed to evaluate if a patient with ischemic heart failure and failed ejection fraction is an appropriate candidate for stem cell therapy and can benefit from it with high probability of cardiac regeneration. The clinical trial depicted a striking difference in cardiac recovery between responders and non-responders, which was associated with a specific signature composition of angiogenesis factors in peripheral blood. Conductance of the clinical study is detailed below.

A study accompanying a controlled, prospective, randomized, double blinded multicenter trial ("Intra-myocardial Transplantation of Bone Marrow Stem Cells in Addition to Coronary Artery Bypass Graft Surgery (PERFECT)"), which was launched in the Rostock University cardiac surgery department was carried out. The trial evaluated efficacy and safety of intra-myocardial CD133$^+$ cell injection in patients with coronary artery disease after myocardial infarction with reduced LVEF and presence of a localized kinetic/hypokinetic/hypoperfused area of the left ventricle. Prior results revealed close relations between some of regenerative factors and response of patients to the therapy (CABG or CABG plus CD133$^+$ stem cells injection). An increase in a minimum of 5% in LVEF, measured by MRI, was selected to designate functional improvement at 6-12 months follow-up. The patients, who increased LVEF more than 5%, are defined as the responders, enhancement of less than 5% or decreased LVEF are defining the non-responders.

Biomarkers

Pre-specified: Distinct hematopoetic and endothelial CD133$^+$ EPC subpopulations and angiogenesis capacity were tested in a cohort of 39 patients in bone marrow (BM) and peripheral blood (PB) employing coexpression analysis using four-laser flow cytometric methods (LSR II, Becton Dickinson, Heidelberg, Germany) for costaining panel enumeration of EPC (co-staining panel CD133, 34, 117, 184, 309, 105, 45) and circulating endothelial cells (CEC) (co-staining panel: CD31, 146, 34, 45, 105, 184, 309) as well as in vitro CFU-EC, CFU-Hill and in vivo Matrigel plug assay. NT-proBNP as well as virus analysis were performed for Epstein-Barr-Virus (EBV), Cytomegalovirus (CMV), and Parvovirus by IgG and antigen analysis in peripheral blood serum. Post hoc analysis before final data closure was performed for serum angiogenesis factors and cytokines. Post hoc analysis: BM subpopulation analysis and SH2B3 mRNA RT-PCR in peripheral blood (PB): Methods and analysis of biomarkers studied in BM CD133+ and PBMNC samples used cytometric bead array (CBA) and enzyme-linked immunosorbent assay (ELISA) and RT-PCR.

Statistical Analysis

The stratification of the primary analysis by centre was neglected in the sample size calculation. Instead of the analysis of covariance (ANCOVA) used in the primary analysis, the two-sample t-test scenario with equal variances was considered. Sample size was determined with the assumption of a two-sided type I error ($\alpha$) at 5% and a type II error ($\beta$) at 10% (i.e. a power at 90%). The scenario of a difference in LVEF at month 6 post-operation between the two treatment arms of 4 to 5% was considered as a clinically relevant difference. With a difference of 4.5 and a standard deviation of 7.5, at least n=60 patients per group were considered necessary and, with an additional 15% drop-out rate, a total of at least 142 patients were to be randomized. Sample size was calculated using the commercial program nQuery Advisor 5.0, section 8, table MTTO-1 (Hofmann W K, de Vos S, Elashoff D, et al., Lancet 2002; 359(9305): 481-6). Computation was realized using central and non-central t-distribution where the non-centrality parameter is $\sqrt{n} \, \delta/\sqrt{2}$ and $\delta$ is defined as effect size $|\mu1-\mu2|/\sigma$ (O'Brien R G, Muller K E, Signified power analysis for t-tests through multivariate hypothesis. In L K Edward (Ed.) Applied analysis of variance in behavioral science, 1993, New York, Marcel Dekker).

Statistical analyses, final data set calculation, and preparation were performed by Koehler GmbH, Data analysis with machine learning identifying key features and classification of the comprehensive patient data was obtained by employing supervised and unsupervised machine learning (ML) algorithms (Kuhn M, J Statistical Software, 2008; 28(5):1-26). The data were pre-processed while removing features with low variance and high correlation for dimension reduction following best practices recommendations. Missing measurements were filled with zeros as frequently used in standard data imputation practices. The following supervised algorithms were compared: AdaBoost, Support Vector Machines (SVM) and Random Forest (RF) (Forman G and Cohen I, 2004. "Learning from Little: Comparison of Classifiers Given Little Training" doi: 10.1007/978-3-540-30116-5_17). Small clinical datasets are often prone to overfitting. Classifiers were employed that are suitable for training on small data sets for a comparison of features given little training and chose the most appropriate algorithm according to accuracy and robustness towards overfitting (Saeb A T, Al-Naqeb D. Scientifica (Cairo). 2016; 2016: 2079704. doi:10.1155/2016/2079704. Epub 2016 May 30). Supervised ML models have been 10-fold cross-validated. Feature selection was then applied from AdaBoost and RF to further reduce the number of features to less than 20. We employed t-distributed stochastic neighbour embedding (t-SNE) for unsupervised machine learning classification and nonlinear dimensionality reduction (Maaten L V D & Hinton G, Visualizing Data using t-SNE. Journal of Machine Learning Research, 2008; 9:2579-2605. Doi http://jmlr.org/papers/v9/vandermaaten08a.html).

Results

Analysis of Patients baseline characteristics in the group of patients for safety set (SAS) and the group of patients per-protocol set (PPS) followed the description of pre-specified cohort analyses SAS (n=77) and PPS (n=58) placebo vs. CD133+. Post hoc analysis was additionally performed to analyse factors influencing primary endpoint outcome. For this, patients were grouped as responders (increase in LVEF>5% at 180 days) or and non-responders (increase in LVEF<5% at 180 days). According to this post hoc analysis 35/58 (60.3%) patients were treatment responders and 23/58 (39.7%) did not improve in LVEF. This responder/non-responder (NR) ratio was similar in the placebo group 57/43% (R/NR: 17/13 patients (pt.)) and in the CD133$^+$ group 64/36% (R/NR: 18/10 pt.), respectively (placebo vs. CD133$^+$: p=0.373).

Efficacy Outcome Analysis

The PPS efficacy analysis group (n=58) was characterized by reduced pump function post MI (measured in MRI at rest) with baseline LVEF 33.5%, SD±6.26% [Min-Max 25-49], n=58. Pre-specified primary endpoint: Six months post treatment the left ventricular function showed a considerable increase in LVEF of +9.6%±SD 11.3% [Min-Max-13-42], p<0.001 (n=58). To discriminate early improvement of left ventricular function by CABG revascularization and late myocardial reverse remodeling, additional intermediate MRI analysis at hospital discharge was available in a subgroup of patients (n=29). This revealed mainly late (day 10-180) increase of ΔLVEF by +6.5%, SD±7.92% [Min-Max-11-23], p=0.007 (n=29). In ANCOVA analysis of the primary endpoint the placebo group improved from baseline LVEF 33.5% to 42.3% at 180 days (ΔLVEF+8.8%, SE±2.17% [CI 38.0, 46.6], p<0.001; n=30) and the CD133⁺ group LVEF was raised from 33.5% to 43.9% (ΔLVEF+10.4%, SE±2.33% [CI 39.0, 48.5], p<0.001; n=28). Treatment group difference CD133⁺ versus placebo with +2.58±SE 3.13% [CI −3.7-8.9], p=0.414 was not statistically significant in ANCOVA analysis. CD133⁺ stem cell group displayed ΔLVEF improvement mainly in the late phase (day 10-180 ΔLVEF) with +8.8%, SD±6.38% [Min-Max 4-10], p=0.001 (n=14) versus placebo controls (day 10-180 ΔLVEF)+4.3%, SD±8.8% [Min-Max−11-23], p=0.077 (n=15).

Responder (R)/Non-Responder (NR)

In post hoc primary endpoint analysis treatment responders were defined as having a ΔLVEF at 180 days versus baseline higher than 5%. The results in dissemination of 35 responders in a cohort of 58 patients were characterized by an overall increase in ΔLVEF in ANCOVA at 180d/0 of +17.1%; SE±2.08% [CI 12.9; 21.3], R vs. NR, p<0.0001 (180d/0), n=58. LVEF increase was +19.1% in CD133⁺ vs. +13.9% in placebo, p=0.099, n=35 (data not shown). In contrast, non-responders showed a ΔLVEF at 180d/0 by 0%, SE±5.73% [CI 22.3; 44.8] p=0.287 (placebo/NR +3.3%, CD133⁺/NR-2.4%).

Post hoc secondary endpoint: Responders showed a significant reduction in LV-dimensions (LVEDV p=0.008, LVESV p=0.0001) and reduction in NT-pro-BNP, p=0.0002 compared to non-responders. This was not reflected by a similar improvement of 6 MWT (p=0.811). The intramyocardial tissue recovery was found in responders with improvement in scar size R vs. NR-8.19 g SE±3.5 g, p=0.0238. CD133⁺ treated NR also displayed reduction in scar size (CD133⁺ NR Δscar size 180d/0: −13.9 g, SD±20.9 g placebo NR +11.9, SD±16.7 g, p=0.008, n=20) and non-viable tissue (Δnon-viable tissue 180d/0: CD133⁺ NR −12.4 g, SD±19.3 g vs. placebo NR +11.5 g, SD±12.0 g, p=0.004, n=19) (data not presented). This tendency was not observed in responders: scar size (CD133⁺ NR vs. placebo NR −1.9, SD±16.0 g vs. placebo +2.5, SD±13.2 g, p=0.398, n=33) and non-viable tissue (CD133⁺ NR vs. placebo NR −1.4, SD±16.7 g vs. placebo +1.8, SD±12.3 g, p=0.544, n=32). Long term survival: The medium term survival was 76.9±3.32 months (R) vs. +72.3±5.0 months (NR), HR 0.3 [CI 0.07-1.2]; p=0.067.

Circulating EPC (CD133⁺/CD34⁺/CD117⁺) in peripheral blood were found to be reduced by a factor of two in NR versus R before treatment. For CD34⁺ MNC subpopulations preoperative blood levels were (R): CD34⁺ 0.072%, SD±0.05% vs. (NR) 0.039%, SD±0.017, RvsNR p=0.027. Similar difference was found preoperatively for CD133⁺, CD133⁺ and CD117⁺ subpopulations (pre-operative. RvsNR: CD133⁺ 0.048%, SD±0.031% vs. 0.021%, SD±0.011%, p=0.005; CD133⁺CD117⁺ 0.019%, SD±0.016% vs. 0.007%, SD±0.008%, p=0.024, n=23) (cf. table 1). This difference was not found for the comparison of placebo and CD133⁺ (placebo vs. CD133⁺ group: CD34⁺ p=0.975; CD133⁺ p=0.995; CD133⁺CD117⁺ p=0.892; n=24) (table 1). In contrast, CD146⁺ CEC showed higher pre-operative levels in non-responders versus responders (p=0.053) (table 1).

Postoperatively, reduction of EPC in NR remained significant until discharge: peripheral blood CD34⁺ (NR vs. R p=0.026 pre-operative and day 10) and CD133⁺ CD117⁺ (NR vs. R p=0.024 pre-operativeop and day 10) despite postoperative increased levels of EPO (NR: preop. 16.9 U/ml, SD±14.1 U/ml; NR day 10: 42.1 U/ml, SD±23.9 U/ml; p=0.006 pre-operative/day 10) and reduction of IP10/CXCL10 (NR pre-operative: 157.6 pg/ml, SD±94.5 pg/ml; NR day 10: 95.8 pg/ml, SD±85.2 pg/ml; p=0.01 pre-operative/day 10).

Treatment responders were characterized pre-operatively by lower serum levels of pro-angiogenic factors such as VEGF (p=0.056 R/NR), EPO (p=0.023 R/NR), CXCL10/IP10 (p=0.076 R/NR), higher levels of IGFBP-3 (p=0.089 R/NR) (table 1), as well as strong induction of VEGF (+26.6 pg/ml, p=0.015 pre-operative/day 10) at day 10 after intervention versus non-responders (+1.2 pg/ml, p=0.913 pre-operative/day 10) (table 1). Isolated bone marrow CD133⁺ cells were all tested positive for their angiogenic potential in vitro by CFU-EC and in vivo by Matrigel plug (data not shown).

Thrombocyte counts were pre-operatively reduced in NR (208×109/L, SD±51.2 109/L [CI 73-311], n=23) versus R (257×109/L, SD±81.5 109/L [CI 123-620], n=35) (NR vs R: p=0.004, n=58) before treatment. Suspecting bone marrow stem cell suppression by finding reduced PB thrombocyte and CD133⁺ CD34⁺ EPC count, we tested RT-PCR gene expression analysis of SH2B3 mRNA coding for the LNK adaptor protein SH2B3 which is associated with inhibition of hematopoietic stem cell response for EPC and megakaryocytes in immediately frozen blood samples. First analysis in 21 patients revealed a tendency of increased mRNA expression in peripheral blood with non-responders (p=0.073) (cf. table 1, FIG. 1).

TABLE 1

Analysis of angiogenesis related biomarkers in blood. Responder versus non-responder and placebo versus CD133⁺ groups were analysed for change in biomarkers of peripheral blood samples between preoperative (Assessment I) and day 10 postoperative (discharge). The data are derived from the patient group (cohort) with complete analysis (per protocol clinical dataset and biomarker). In this cohort all samples were immediately processed to avoid any change of the samples due to storage or transport. Data are expressed as mean values ± Standard deviation, P-value between time point 0 and 10 days, P^A-value between responder/non-responder, stem cell/control for each time point (PB—peripheral blood, EPO—erythropoietin).

| | | Responder versus Non-Responder | | | | |
|---|---|---|---|---|---|---|
| Biomarker (peripheral blood, unit) | Time point | Responder (n = 15) | P 10 days vs 0 | Non-responder (n = 8) | P 10 days vs 0 | P^A R vs NR |
| SH2B3 mRNA (ΔCT %) | 0 | −1.17 ± 0.28 | ... | −1.56 ± 0.51 | ... | 0.073 |
| CD34 (% MNC) - EPC | 0. 10 d | 0.072 ± 0.05 0.059 ± 0.048 | 0.197 | 0.039 ± 0.017 0.027 ± 0.01 | 0.116 | 0.027 0.026 |

TABLE 1-continued

Analysis of angiogenesis related biomarkers in blood. Responder versus non-responder and placebo versus CD133+ groups were analysed for change in biomarkers of peripheral blood samples between preoperative (Assessment I) and day 10 postoperative (discharge). The data are derived from the patient group (cohort) with complete analysis (per protocol clinical dataset and biomarker). In this cohort all samples were immediately processed to avoid any change of the samples due to storage or transport. Data are expressed as mean values ± Standard deviation, P-value between time point 0 and 10 days, $P^A$-value between responder/non-responder, stem cell/control for each time point (PB—peripheral blood, EPO—erythropoietin).

| | | | | | | |
|---|---|---|---|---|---|---|
| CD133 (% MNC) - EPC | 0 | 0.048 ± 0.031 | 0.245 | 0.021 ± 0.011 | 0.932 | 0.005 |
| | 10 d | 0.041 ± 0.039 | | 0.021 ± −0.013 | | 0.105 |
| CD133, 117 (% MNC) EPC | 0 | 0.019 ± −0.016 | 0.421 | 0.007 ± 0.008 | 0.765 | 0.024 |
| | 10 d | 0.022 ± 0.024 | | 0.006 ± 0.004 | | 0.024 |
| CD146 (% MNC) - CEC | 0 | 1.1 ± 0.57 | . . . | 2.2 ± 1.3 | . . . | 0.053 |
| | 10 d | 1.72 ± 1.73 | | 1.86 ± 1.53 | | 0.853 |
| IGFBP-3 (ng/ml) | 0 | 2121.9 ± 487.1 | 0.115 | 1623.7 ± 651.4 | 0.257 | 0.089 |
| | 10 d | 1753.6 ± 830.8 | | 1378.4 ± 518.7 | | 0.261 |
| VEGF (pg/ml) | 0 | 24.6 ± −36.6 | 0.015 | 39.6 ± 33.4 | 0.913 | 0.056 |
| | 10 d | 51.2 ± 55.8 | | 40.8 ± −44.5 | | 0.528 |
| IP-10 (pg/ml) | 0 | 96.7 ± 42.6 | 0.04 | 157.6 ± 94.5 | 0.01 | 0.076 |
| | 10 d | 63.3 ± 28.3 | | 95.8 ± 85.2 | | 0.324 |
| EPO (mIU/ml) | 0 | 5.9 ± 3.7 | 0.001 | 16.9 ± 14.1 | 0.006 | 0.023 |
| | 10 | 60.1 ± 27.7 | | 42.1 ± 23.9 | | 0.180 |

Placebo versus CD133+

| Biomarker (peripheral blood, unit) | Time point | Stem cell (n = 11) | P | Control (n = 13) | P | $P^A$ |
|---|---|---|---|---|---|---|
| SH2B3 mRNA (ΔCT %) | 0 | −1.35 ± 0.45 | . . . | −1.29 ± 0.41 | . . . | 0.756 |
| CD34 (% MNC) - EPC | 0. | 0.062 ± 0.037 | 0.128 | 0.064 ± 0.053 | 0.250 | 0.975 |
| | 10 d | 0.041 ± 0.038 | | 0.058 ± 0.047 | | 0.363 |
| CD133 (% MNC) EPC | 0 | 0.04 ± 0.03 | 0.338 | 0.04 ± 0.029 | 0.619 | 0.995 |
| | 10 d | 0.032 ± 0.026 | | 0.038 ± 0.032 | | 0.637 |
| CD133, 117 (% MNC) - EPC | 0 | 0.014 ± 0.013 | 0.902 | 0.016 ± 0.017 | 0.265 | 0.892 |
| | 10 d | 0.015 ± 0.02 | | 0.019 ± 0.022 | | 0.626 |
| CD146 (% MNC) - CEC | 0 | 1.53 ± 1.33 | . . . | 1.481 ± 0.67 | . . . | 0.919 |
| | 10 d | 1.64 ± 1.55 | | 1.87 ± 1.74 | | 0.750 |
| IGFBP-3 (ng/ml) | 0 | 1950.6 ± 689.9 | 0.139 | 1946.8 ± 507 | 0.231 | 0.972 |
| | 10 d | 1561.6 ± 783.2 | | 1679.4 ± 742.6 | | 0.715 |
| VEGF (pg/ml) | 0 | 30.2 ± 29.1 | 0.142 | 29.6 ± 39.1 | 0.124 | 0.961 |
| | 10 d | 55.8 ± −58.5 | | 38.5 ± 44.7 | | 0.293 |
| IP-10 (pg/ml) | 0 | 129.2 ± 96.7 | 0.011 | 102.9 ± 34.6 | 0.001 | 0.275 |
| | 10 d | 83.2 ± 77.9 | | 64.5 ± 22.7 | . . . | 0.457 |
| EPO (mIU/ml) | 0 | 7.7 ± 3.1 | 0.001 | 10.3 ± 12.6 | 0.001 | 0.561 |
| | 10 d | 53.5 ± −30.6 | | 56.4 ± 25.5 | | 0.814 |

To identify a diagnostic response signature for R/NR we used machine learning methods as a tool for the prediction of functional improvement after cardiac stem cell therapy and CABG surgery. First analyses were performed to particularly exclude overfitting in small populations. Then, blinded patient data from the PERFECT clinical database was investigated by, unsupervised ML, which is able to cluster similar patients in close proximity and reveals distinct groups. Investigating the underlying segmentation, the firstline supervised ML analysis was made for all time points to place patient characteristics into two distinct groups. The calculation independently assigned patient characteristics according to ΔLVEF at 180 days confirming the pre-selection criteria of >5% (cf. table 2, FIG. 2).

Then machine learning algorithms were used to investigate the decisive parameters to a response signature. For this the underlying PERFECT clinical dataset and biomarker laboratory measurements were combined and analysed to validate classification specificity of parameter profiles for responders and non-responders before and after the CABG procedure. In particular, we used discriminative primary and secondary endpoint parameters as well as thrombocyte and leukocyte counts. Using only the clinical parameters (n=160) classification resulted in a specificity of responders assuming mean accuracy of 63.35% (180 days) (table 2). Combination of preoperative clinical data (n=49) and biomarker laboratory parameters (n=142), however, revealed higher sensitivity of angiogenesis/EPC/CEC related parameters in peripheral blood already preoperative with respective assuming max accuracy of 81.64%±SE 0.51% [CI 80.65-82.65] (n=31) (table 2). Interestingly, 17/20 relevant parameters were related to angiogenesis parameters, bone marrow EPC/CEC responses, NTproBNP, and SH2B3 gene expression in peripheral blood (table 2). Using both clinical and biomarker parameters preoperative prediction accuracy for responders was 79.35%±SE 0.24% [CI 78.87-79.84] (n=31) and for non-responders 83.95%±SE 0.93% [CI 82.10-85.80] (n=31). Postoperative evaluation at day 10 (n=382) revealed a prediction accuracy of 82.12%±SE 0.28% [CI 81.56-82.67] (n=31) (R) and 85.89%±SE 0.67% [CI 84.56-87.22] (n=31) (NR), while day 0-180 combined clinical and biomarker analysis (n=522) allowed a prediction accuracy of 94.77%±SE 0.43% [CI 93.92-95.63] (n=31) (R) and 92.44%±SE 0.60% [CI 91.24-93.64] (n=31) (NR) (cf. FIG. 3).

Feature selection based on our machine learning approach led to the identification of decisive factors for lack of response and the induction of cardiac regeneration, which can be used for diagnostic R/NR selection before and monitoring of during treatment. The core factors for laboratory diagnosis in peripheral blood were NT-proBNP, VEGF, erythropoietin, vitronectin, circulating EPC/CEC/Thrombocytes, SH2B3 mRNA expression, the CFU-Hill assay/Matrigel plug for peripheral blood, as well as weight and LVESV index. We found a statistical correlation of the identified factors and calculated their diagnostic use for the selection of responder and non-responder patients using repeated cross-validation (cf. FIG. 4).

A laboratory biomarker subset was selected together with specific features of the clinical trial by ML. The computationally selected features and biomarkers are depicted in table 2 below. Accuracy of prediction was determined above 80%.

TABLE 2

Machine learning selected parameters for diagnostic discrimination of responders and non-responders.

| Computationally selected features for the clinical trial data and laboratory biomarker subset of the Rostock group (day 0 - preoperative) N = 31 | Weights for the selected Features |
|---|---|
| NT proBNP | 9 718 |
| VEGF | 7 810 |
| Erythropoietin | 4 262 |
| Vitronectin | 3 898 |
| CFU_Hill | 2 871 |
| CD45Neg_EPC | 2 186 |
| CD117_184_PB_EPC_IHG | 2 146 |
| CD45_117_184_EPC | 2 118 |
| CD45_133_146_PB_CEC | 1 969 |
| Thrombocytes | 1 951 |
| IGFBP-3 | 1 922 |
| CD133 pro ml PB_IHG | 1 910 |
| CD146_PB_CEC | 1 799 |
| CD105_PB_CEC | 1 793 |
| CD45_133_34_105_PB_CEC | 1 489 |
| MatrigelPlug_PB_31 | 1 475 |
| CD45_133_34_117_309_EPC | 1 420 |
| Delta_CT_SH2B3 | 1 393 |
| Weight | 1 363 |
| LVESV | 1 352 |
| Accuracy: | 81 64% |

The invention illustratively described herein suitably may be practised in the absence of any element or elements, limitation or limitations which is/are not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

All references cited in this specification are herewith incorporated by reference with respect to their entire disclosure content and the disclosure content specifically mentioned in this specification.

ABBREVIATION CODE

AE=Adverse Event
AESI=Adverse Event of Special Interest
AHA=American Heart Association
ANCOVA=Analysis of covariance
BM=Bone marrow
BMSC=Bone marrow stem cells
CABG=Coronary Artery Bypass Graft
CAP-EPC=Concentrated Ambient Particles—Endothelial Progenitor Cells
CBA=Cytometric Bead Array
CCS=Canadian Cardiovascular Society
CCTRN=Cardiovascular Cell Therapy Research Network
CD=Cluster of Differentiation
CEC=Circulating endothelial cells, CEC panel, CDs measured in PB
CFU=Colony-forming unit
CI=Confidence interval
CMV=Cytomegalovirus
EA=Early Antigen
EBNA1=EBV-Nuclear Antigen 1
EBV=Epstein-Barr-Virus
EC=Endothelial Cells
ECG=Echocardiography
ELISA=Enzyme-Linked Immunosorbent Assay
EPC=Endothelial Progenitor Cells, EPC panel, CDs measured in PB
EPO=Erythropoietin
GMP=Good Manufacturing Practice
HR=Hazard ratio
HIF=Hypoxia-Inducible Factor, transcription factor
ICH GCP=Tripartite Guidelines Guideline for Good Clinical Practice
IGF-1=Insulin-like Growth Factor 1
IGFBP2/3=Insulin-like Growth Factor-Binding Protein 2/3
IHG=Analysis performed in accordance with ISHAGE guidelines
IL=Interleukin
IP-10=Interferon Gamma-induced Protein 10 also known as C-X-C motif chemokine 10 (CXCL10)
LMCA=Left Main Coronary Artery
LVEDV=Left Ventricular End Diastolic Volume
LVEF=Left Ventricular Ejection Fraction
LVESD=Left Ventricular End Systolic Dimension
MACE=Major Adverse Cardiovascular Events
ML=Machine learning
MNC=Mononuclear cells
MRI=Magentic Resonance Imaging
6MWT=6-Minute Walk Test NT-proBNP=B-type Brain Natruretic Peptide
PB=Peripheral blood
PBMNC=mononuclear cells isolated from peripheral blood
PCI=Percutaneous Coronary Intervention
PEI=Paul-Ehrlich Institute
PPS=Group of patients for per-protocol set
SAE=Serious adverse event
SAS=Group of patients for safety set
SDF-1=Stromal Cell-derived Factor 1
SH2B3=Lnk [Src homology 2-B3 (SH2B3)] belongs to a family of SH2-containing proteins with important adaptor functions
SCF=Stem Cell Factor
STEMI=ST—segment Elevation Infarction
SUSAR=Suspected Unexpected Serious Adverse Reaction
TNF=Tumor Necrosis Factor
t-SNE=t-distributed stochastic neighbour embedding
VCA=Virus-Capsid-Antigen
VEGF=Vascular Endothelial Growth Factor
VEGF rec=Vascular Endothelial Growth Factor Receptor
VEGFR2/KDR=Vascular Endothelial Growth Factor Receptor 2/Kinase Insert Domain Receptor

The invention claimed is:

1. A method for prediction of response to stem cell therapy for coronary artery disease or ischemic vascular disease, wherein the method comprises
   (i) determining in a sample of a subject the amount of each of the following biomarkers, wherein the biomarkers include each of a growth factor selected from the group consisting of vascular endothelial growth factor (VEGF), Erythropoietin, and FGF, lymphocyte adapter protein, a glycoprotein selected from the group consisting of Vitronectin and granulocyte-colony stimulating factor (GCSF), brain natriuretic peptide (BNP), circulating endothelial progenitor cells (EPC), circulating endothelial cells (CEC), circulating thrombocytes, and circulating mononuclear cells and subpopulations,
   (ii) comparing the total determined amounts of all of the biomarkers in the sample to a baseline value and/or a reference of biomarkers obtained from subjects who had undergone stem cell therapy for coronary artery disease and categorized into responders or nonresponders to the stem cell therapy, and
   (iii) predicting, whether a response to stem cell therapy in the subject is to be expected based on whether the total determined amounts of the biomarkers in the sample are more similar to the baseline value and/or reference of the biomarkers obtained from the responders than that of the nonresponders, or whether a response to stem cell therapy in the subject is not expected based on whether the total determined amounts of the biomarkers in the sample are more similar to the baseline value and/or reference of the biomarkers obtained from the nonresponders than that of the responders.

2. The method according to claim 1, wherein the sensitivity of prediction accuracy is more than about 80%, and the specificity of prediction accuracy is more than about 80%.

3. The method according to claim 1, wherein the growth factor is selected from the group consisting of VEGF and Erythropoietin, the glycoprotein is Vitronectin and the brain natriuretic peptide is NT-proBNP.

4. The method according to claim 1, wherein the method uses further biomarkers, wherein the further biomarkers are selected from the group consisting of Cytokine, Interleukin, Interferon, Insulin-like-growth-factor-binding protein, Insulin-like growth factor, Chemokine protein and/or Multi-protein E3 ubiquitin ligase complex.

5. The method according to claim 4, wherein the Cytokine is TNF, the Interleukin is selected from the group consisting of IL-6, IL-8, and IL-10, the Interferon is human interferon gamma-induced protein 10, the Insulin-like-growth-factor-binding protein is selected from the group consisting of Insulin-like-growth-factor-binding protein-2 and Insulin-like-growth-factor-binding protein-3, the Insulin-like growth factor is IGF2, the Chemokine protein is SDF-1 and/or the Multi-protein E3 ubiquitin ligase complex is SCF.

6. The method according to claim 1, wherein the method is also used for prediction of response to induction of angiogenesis; response to tissue repair of a cardiovascular disease including myocardial infarction, stroke, peripheral ischemic vascular disease, or heart disease; or response to ischemic preconditioning.

7. The method according to claim 6, wherein the stem cell therapy comprises transplantation of CD133 positive stem cells.

8. The method according to claim 6, wherein the stem cell therapy is accompanied by coronary artery bypass graft (CABG).

9. The method according to claim 1, wherein the sample is taken from a subject suffering from heart disease and/or arteriosclerosis.

10. The method according to claim 1, wherein the method comprises profiling of the results of the comparison of at least two, three, four, five, six or more time points.

11. The method according to claim 10, wherein the sensitivity of prediction accuracy is more than 90%, and the specificity of prediction accuracy is more than 90%.

12. The method according to claim 1, wherein the method further comprises the use of clinical diagnostic parameters.

13. The method according to claim 1, wherein the method is used for profiling of angiogenesis response.

14. The method according to claim 1, wherein the method further comprises analysing an RNA and/or mRNA sequence and/or functional RNA and/or non-coding RNA and/or single nucleotide polymorphism (SNP) comprising a diagnostic signature.

15. The method according to claim 1, wherein the method further comprises analysis of pharmacokinetic and pharmacogenetic data employing RNA and/or DNA sequencing analysis and/or network pathway analysis.

16. The method according to claim 1, wherein the method further comprises analysis of phenotyping.

17. The method according to claim 1, wherein said subject is a human.

18. The method according to claim 1, wherein said sample is a blood, a serum and/or a plasma sample, and/or a tissue biopsy sample and/or a sample of circulating stem cells.

* * * * *